(12) United States Patent
Nozaki et al.

(10) Patent No.: US 7,031,847 B1
(45) Date of Patent: Apr. 18, 2006

(54) METHOD AND APPARATUS FOR DISPLAYING GENE EXPRESSION PATTERNS

(75) Inventors: Yasuyuki Nozaki, Kanagawa (JP); Ryo Nakashige, Kanagawa (JP); Tsunehiko Watanabe, Kanagawa (JP); Takuro Tamura, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 09/677,042

(22) Filed: Sep. 29, 2000

(30) Foreign Application Priority Data

Sep. 30, 1999 (JP) .............................. 1999/277918
Mar. 28, 2000 (JP) .............................. 2000/088695

(51) Int. Cl.
*G96F 7/06* (2006.01)
*G06N 7/00* (2006.01)

(52) U.S. Cl. ............................... 702/20; 702/19; 703/2

(58) Field of Classification Search .................. 702/19, 702/20; 703/2; 707/104.1
See application file for complete search history.

(56) References Cited

U.S. PATENT DOCUMENTS 5,889,523 A     3/1999   Wilcox et al.
6,263,287 B1 *  7/2001   Zheng et al. .................. 702/20

OTHER PUBLICATIONS

Perou et al. Distinctive gene expression patterns in mammary epithelial cells and breast cancers. PNAS (Aug. 1999) vol. 96, pp. 9212-9217.*
Wen et al. Large-scale temporal gene expression mapping of central nervous system development. PNAS (Jan. 1998) vol. 95, pp. 334-339.*
Eisen, et al. (1998) Proc. Natl. Acad. Sci. USA 95(25): 14863-8.
Guatam Das, King-Ip Lin, Heikki Mannila, Gopal Renganathan and Padhraic Smyth, "Rule Discovery From time Series", Proceedings Fourth International Conference on Knowledge Discovery and Data Mining, Aug. 27-31, 1998, pp 16-22.
Lamonn J. Keogh and Michael J. Pazzant, "Scaling Up Dynamic Time Warping to Massive Datasets", Principles of Data Mining and Knowledge Discovery, Third European Conference. PKDD'99, pp. 1-11.
Michael B. Easm, Paul T. Spellman, Patrick O. Brown and David Botstem, "Cluster Analysis and Display of Genome-Wide Expression Patterns", Proc. National Academy of Science:, Proceedings of the National Academy of Sciences of USA. National Academy of Science, Washington. US. vol. 95, Dec. 1998, pp. 14863-14868.
Irving Hofman and Ray Jarvis, "Robust and Efficient Cluster Analysis Using a Shared Near Neighbours Approach", Pattern Recognition, 1998 Proceedings, Fourteenth International Conference on Brisbane, QLD., Australia 16-20 Aug. 1998, Lost Alamitos. CA. IEEE Comput. Soc. Aug. 16, 1998, pp. 243-247.
"Description of Pirouette Algorithms", Chemometrics Technical Note, 1993, pp. 1-4.
EPO Search Report addressed to the corresponding EP App. No. 00121116.8 dated Jul. 17, 2003.

* cited by examiner

*Primary Examiner*—Marjorie A. Moran
(74) *Attorney, Agent, or Firm*—Reed Smith LLP; Stanley P. Fisher, Esq.; Juan Carlos A. Marquez, Esq.

(57) ABSTRACT

The present invention discloses a method for displaying gene expression patterns of multiple genes that change according to the experiment cases, where a first axis represents the genes and a second axis represents the experiment cases. The method comprises two steps. The first step consists of designating a segment along the second axis in the expression pattern data of the multiple genes. The second step comprises clustering the expression pattern data within the designated segment along the second axis based on a predetermined reference value, repeating clustering within the same cluster in a forward or reverse direction along the second axis while changing the reference value, and displaying the results according to a predetermined display format.

11 Claims, 26 Drawing Sheets

201; Clustering-applied region

201; Clustering-applied region

Exemplary display of the results of clustering analysis

FIG.14

Example of gene expression pattern data

| Gene ID (geneID) | Experiment cases | | | | | | | | | |
|---|---|---|---|---|---|---|---|---|---|---|
| | 1 | 2 | 3 | 4 | 5 | 6 | ·· | ·· | ·· | n |
| 1 | 0 | 1 | 2 | 0 | 3 | 2 | 0 | | | |
| 2 | 1 | 2 | 0 | 0 | 2 | 2 | 1 | | | |
| ⋮ | | | | | | | | | | |
| m | 0 | 4 | 3 | 6 | 5 | 4 | 0 | | | |

1401

1402 m number of vector data

Example of cluster structures

| cluster | |
|---|---|
| Members | Value |
| type | leaf |
| left | |
| right | |
| distance | |
| geneID | 17 |
| level | 0 |

1501

| cluster | |
|---|---|
| Members | Value |
| type | node |
| left | ● |
| right | ● |
| distance | 91 |
| geneID | |
| level | 5 |

→ cluster L
→ cluster R

1502

Exemplary structure of cluster tree

Detailed flowchart of clustering analysis (1: Generating cluster tree)

Detailed flowchart of clustering analysis (2: Setting cluster levels)

Detailed flowchart of clustering analysis (3: Generating display data)

Flowchart of generating display data (Process A)

Exemplary display of standard clustering analysis

An exemplary display of the entire results of clustering analysis and a corresponding display of the targeted cluster tree

METHOD AND APPARATUS FOR DISPLAYING GENE EXPRESSION PATTERNS

FIELD OF THE INVENTION

The present invention relates to a method and an apparatus for displaying gene expression patterns resulting from hybridization with a specific gene at certain time points in a display format (or an output format) that displays the patterns in a visually apprehensible manner so that the functions and roles of the genes can easily be studied.

BACKGROUND OF THE INVENTION

With the increase in the number of species that have been determined of their genome sequences, so called genome comparison has extensively been performed. Genome comparison aims at finding something based on gene difference among species, for example, finding genes involved in evolution, finding a collection of genes which are considered to be common to all species, or conversely studying the nature unique to specific species.

The recent development of infrastructures such as DNA chips and DNA microarrays has changed the interest in the art of molecular biology from information of interspecies to information of intraspecies, namely coexpression analysis, and broadened the study covering from extraction of information to correlation of information, including the conventional comparison between species.

For example, if an unknown gene has an expression pattern identical to that of a known gene, the unknown gene can be assumed to have a similar function to that of the known gene. Such functional meanings of genes and proteins are studied as function units or function groups. The interactions between the function units or function groups are also analyzed by correlating with known enzymatic reaction data or metabolism data, or more directly, by knocking out or overreacting a specific gene to eliminate or accelerate expression of the gene to study the direct and indirect influences on the gene expression patterns of the whole collection of genes.

One successful case in this art field is the expression analysis of yeast by the group of P. Brown from the Stanford University (Michel B. Eisen et al., Clustering analysis and display of genome-wide expression patterns, *Proc. Natl. Acad. Sci.* (1998), Dec 8; 95(25): 14863-8). They hybridized genes with a gene extracted from a cell in a time series using a DNA microarray and numerated the expression levels thereof (i.e., numerated the brightness of the hybridized fluorescent signals). By converting the values into colors, the expression pattern of each gene can be displayed in a visually apprehensible manner. At this point, genes that have a similar expression pattern during their gene cycles (genes having closer expression levels at the same point) are clustered together.

FIG. 24 is a diagram showing an example of displaying expression status 2400 of genes according to the above-described method, where the horizontal and vertical axes indicate time and genes, respectively. In this display, genes belonging to a common cluster may be considered to have common functional characteristics. In FIG. 24, each of the blocks 2401 represents expression status of a gene at one time point. In the figure, the expression status is schematically represented in a gray scale format.

FIG. 25 is a diagram showing an example of displaying expression status 2500 of genes according to the above-described method, where the horizontal and vertical axes indicate experiment cases and genes, respectively. A dendrogram shown on the left is made by stepwisely joining every two most similar clusters together. The length of each branch corresponds to the distance between the two joined clusters. In FIG. 25, each of the blocks 2501 represents an expression status of a gene at one time point. In the figure, the expression status is schematically represented in a gray scale format.

The above-described displaying method allows a supposition that genes belonging to the same cluster may possibly share common functional characteristics.

With the gene expression patterns, however, it is not so simple as to elucidate the relationship among all of the genes in a cell by finding some gene groups having similar expression patterns for the entire cell cycle.

For example, different genes may exhibit similar expression for having similar function at a certain time point. However, they may have different roles at other time point, at which point, of course, the expressions are different. According to the conventional method in which similar expression patterns are clustered together over the entire cell cycle, these genes are classified into different clusters. Therefore, it is difficult to find the above-mentioned characteristics.

In an actual analysis of gene expression patterns, enormous amount of data will be subjected to clustering as shown in FIG. 25. The number of genes is several thousands to ten-thousands, or more than hundred-thousands at maximum. The experiment cases (data) employed may be of any number, for example, in an order of about ten to tens or hundreds. Thus the dendrogram shown in FIG. 25 will be very complicated, containing vast numbers of small branches.

FIG. 26 shows such a complicated case. The left part of FIG. 26 shows the entire results of clustering, targeting mass data of gene expression patterns. The right part of FIG. 26 surrounded by a dotted line 2601 shows the results in a particular region enclosed in a window determined by a user to actually see a narrowed part of the entire results in more detail.

The thus-obtained dendrogram 2602 represents the precise course of joining the most similar clusters. However, it is difficult for the user to find out how many clusters have briefly been classified by looking at this display to judge and guess the groupings of the genes.

It would be useful for the user if the system can suggest the possible cases of the number of the clustering groups so that the user can select the most suitable clustering level. Specifically, data are automatically calculated into groups for various levels of clustering (e.g., 7, 28, 105 and 372 clusters) so that the user may be able to study the grouping of the genes by selecting, from the menu of clustering levels, the suitable results of grouping closer to the desirable level of clustering.

The present invention has an objective of solving such conventional art problems by providing a method and an apparatus for effectively displaying gene expression patterns by finding different genes exhibiting similar expression for having the same function at one time point but having different roles at a different time point.

The present invention also has an objective of providing a method and an apparatus for displaying gene expression patterns by automatically extracting brief groupings of clusters from the results of clustering so that a user can select a desirable level of the grouping for more comprehensible display to study the groupings of the genes. In other words, the present invention has an objective of providing a method and an apparatus for effectively displaying gene expression patterns by providing multiple selectable clustering levels.

SUMMARY OF THE INVENTION

In order to achieve the above-described objectives, the present invention provides a method for displaying gene expression pattern for visually displaying time sequential expression patterns of multiple genes whose expressions change according to experiment cases where a first axis represents the genes and a second axis represents the experiment cases, the method comprising the steps of: designating a segment along the second axis in the expression pattern data of the multiple genes; and clustering the expression pattern data within the designated segment along the second axis based on a predetermined reference value, repeating clustering within the same cluster in a forward or reverse direction along the second axis while changing the reference value, and displaying the results according to a predetermined display format.

The reference value refers to value for determining whether expression patterns of distinct genes are the same or different.

Furthermore, the present invention displays two or more different genes according to the predetermined display format where they have the same expression pattern at the beginning but become to have different expression patterns within the segment along the second axis.

The present invention also displays two or more different genes according to the predetermined display format where they have different expression patterns at the beginning but become to have the same expression pattern within the segment along the second axis.

The experiment cases may be time sequential experiments, states of individual's tissue, species of individuals, individual's sites, or presence and absence of an artificial condition. Alternatively, the experiment cases may be combinations of some of the group consisting of time sequential experiments, states of individuals tissue, species of individuals, individual's sites, and presence and absence of an artificial condition.

The present invention is also an apparatus for analyzing gene expression patterns, which acquires, from a database, expression pattern data of multiple genes whose expressions change according to experiment cases, and which visually displays the expression patterns on a screen of a display device where a first axis represents the genes and a second axis represents the experiment cases, the apparatus comprising:

an inputting means for designating a segment along the second axis in the expression pattern data of the multiple genes obtained from the database; and an arithmetic unit for clustering the expression pattern data within the designated segment along the second axis based on a predetermined reference value, repeating clustering within the same cluster in a forward or reverse direction along the second axis while changing the reference value, and displaying the results according to a predetermined display format.

In order to achieve the above-described objectives, the present invention comprises a step of displaying a round number of the cluster groups for each clustering phase taking a recognition error range in consideration, for the results of the clustering analysis of the gene expression pattern data.

For example, the results of the analysis at multiple phases are stored regardless of the recognition error range input by a user so that the user can choose the briefness of the analysis results to be displayed from multiple phases presented.

In displaying the results, a phase scale bar and a dendrogram cross-cutting line are provided for selecting the phase from the multiple phases. The user can select a specific result at a desirable phase by moving the dendrogram cross-cutting line on the phase scale bar. Upon moving the dendrogram cross-cutting line on the phase scale bar, the number of gene groups (clusters) at that phase. Moreover, dividing lines for distinguishing the gene groups at that phase are displayed, and the gene groups of a predetermined size are specified.

This specification includes part or all of the contents as disclosed in the specifications and/or drawings of Japanese Patent Applications Nos. 11-277918 and 2000-88695 which are priority documents of the present invention.

BRIEF DESCRIPTION OF THE DRAWINGS

FIG. 14 is a schematic diagram showing an exemplary structure of gene expression pattern data.

DESCRIPTION OF THE PREFERRED EMBODIMENTS

Hereinafter, the present invention will be described in more detail with reference to the accompanying drawings. In the following example, time sequential experiments are exemplified as typical experiment cases.

Figure 1:
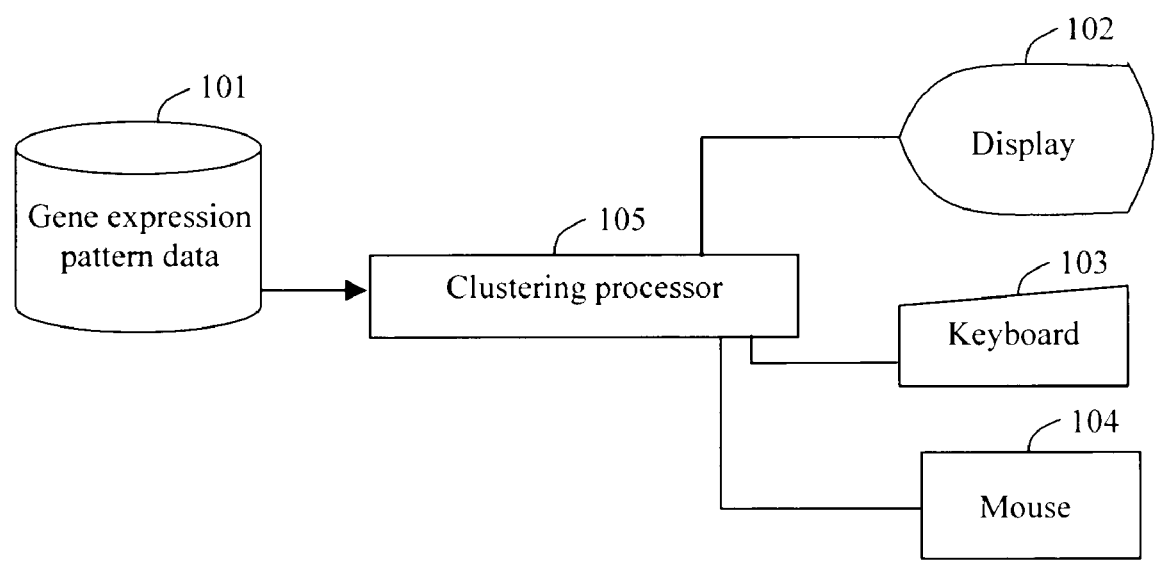
FIG. 1 is a schematic view showing one embodiment of an analyzing apparatus according to the present invention.

FIG. 1 is a schematic view showing a system structure of one embodiment of an apparatus for analyzing gene expression patterns, which employs a method of the invention for displaying gene expression patterns. The analyzing apparatus of this embodiment is provided with a storage medium (or database) 101 for storing data of gene expression patterns obtained by numerating the levels of gene expressions obtained during a series of cell process, a display 102 for visualizing and displaying the data of expression patterns, a keyboard 103 and a mouse 104 for inputting values into the system or for selection, and a clustering processor 105 for clustering the expression pattern data along the course of gene expressions. The clustering processor 105 is embodied with a computer and a program therefor.

An alternative embodiment is configured such that the data of gene expression patterns is acquired from, instead of the storage medium 101, database supervised by a remotely provided server computer via a network or the like.

According to this embodiment, a time segment is designated among the cell cycle to perform clustering within this time segment in a small range.

Figure 2:
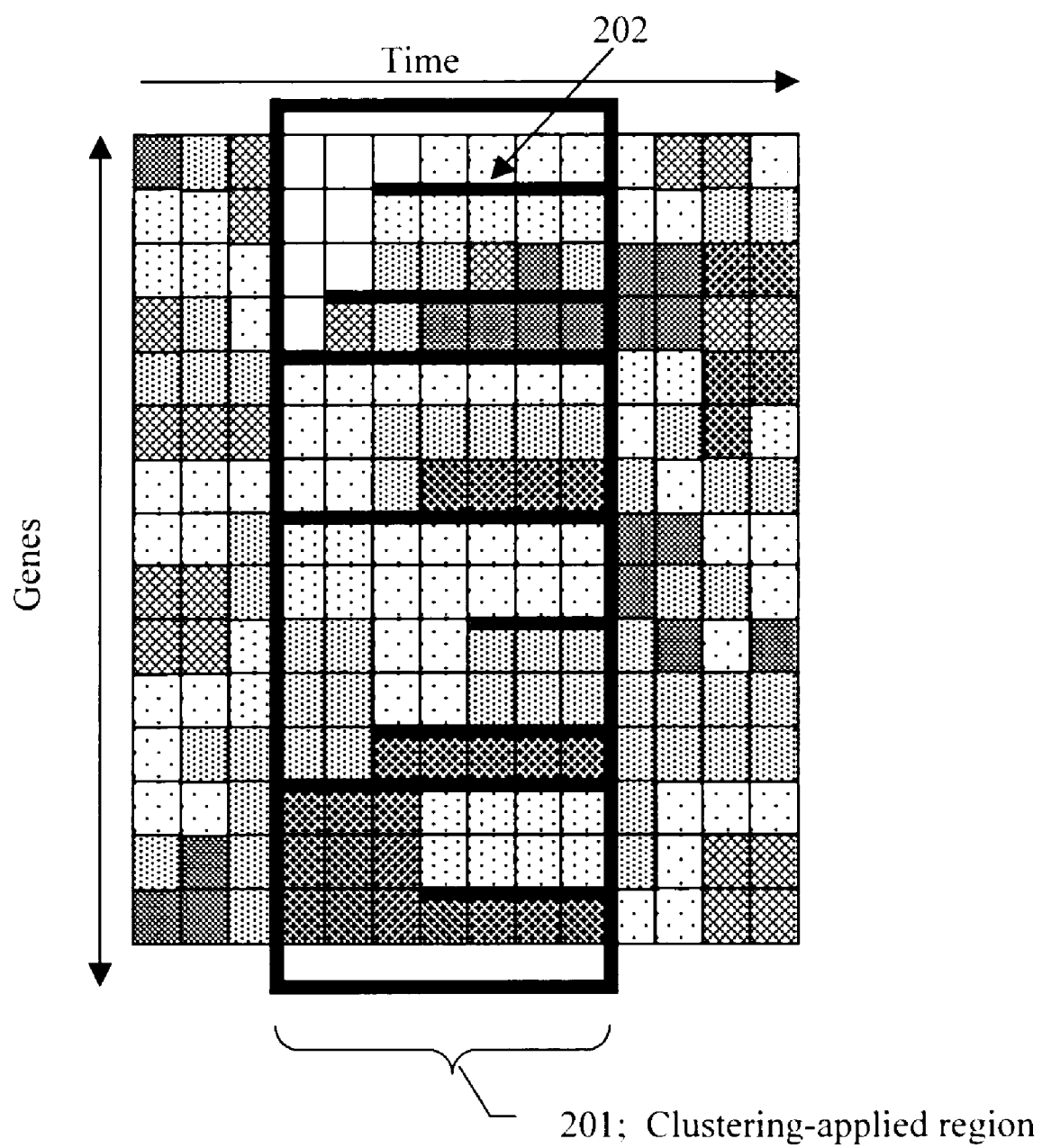
FIG. 2 is a schematic view showing one example of gene expression pattern where a narrowed region has been subjected to clustering in a small range. (in forward time direction)

Specifically, genes belonging to the same cluster are gathered together and a dividing line is drawn between distinctive clusters. Clustering is further performed for the genes belonging to the same cluster. As shown in FIG. 2, when clustering is repeatedly performed in small range from the beginning of the clustering-applied region in the forward direction along the time axis, the course of gene expressions can be expressed as a tree structure. In FIG. 2, the designated time segment is shown as a clustering-applied region 201.

In other words, the expression patterns within the clustering-applied region are arranged that they have the same expression levels at the beginning but become different at some point in the time segment. When such a display is obtained, it can be assumed that different genes exhibited similar expressions at the beginning for having the same function, but became to give different expressions at some time point for having different roles.

Figure 3:
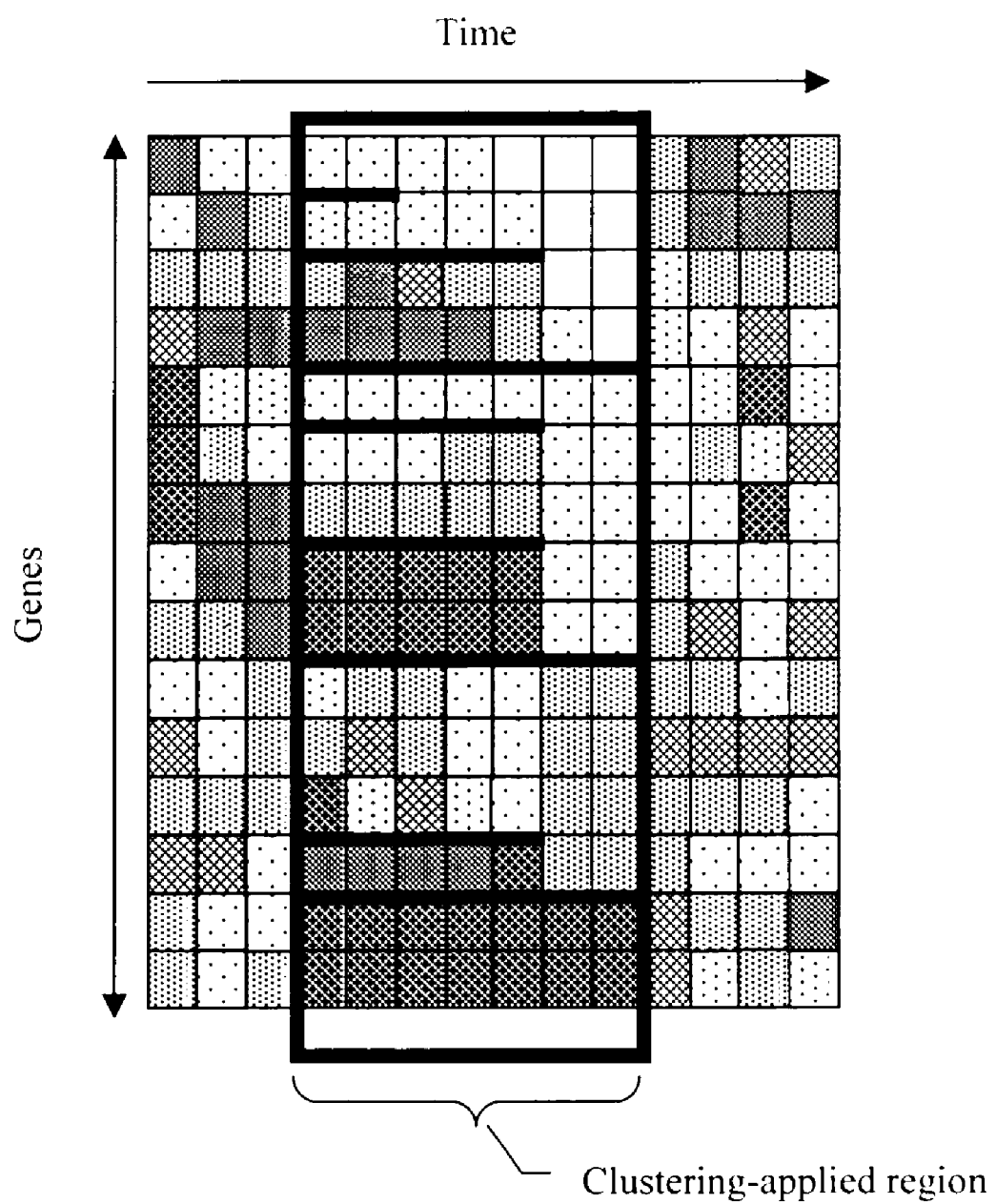
FIG. 3 is a schematic view showing another example of gene expression pattern where a narrowed region has been subjected to clustering in a small range. (in reverse time direction).

Similarly, when small-range clustering is performed from the end of the clustering-applied region in reverse time direction, the gene expression patterns may be arranged into a reverse-tree structure as shown in FIG. 3.

This display indicates expression patterns that are different at the beginning of the region but become the same at some point in the time segment. It can be assumed that, in this case, different genes have different functions at the beginning but at some time point become to have similar roles.

Figure 4:
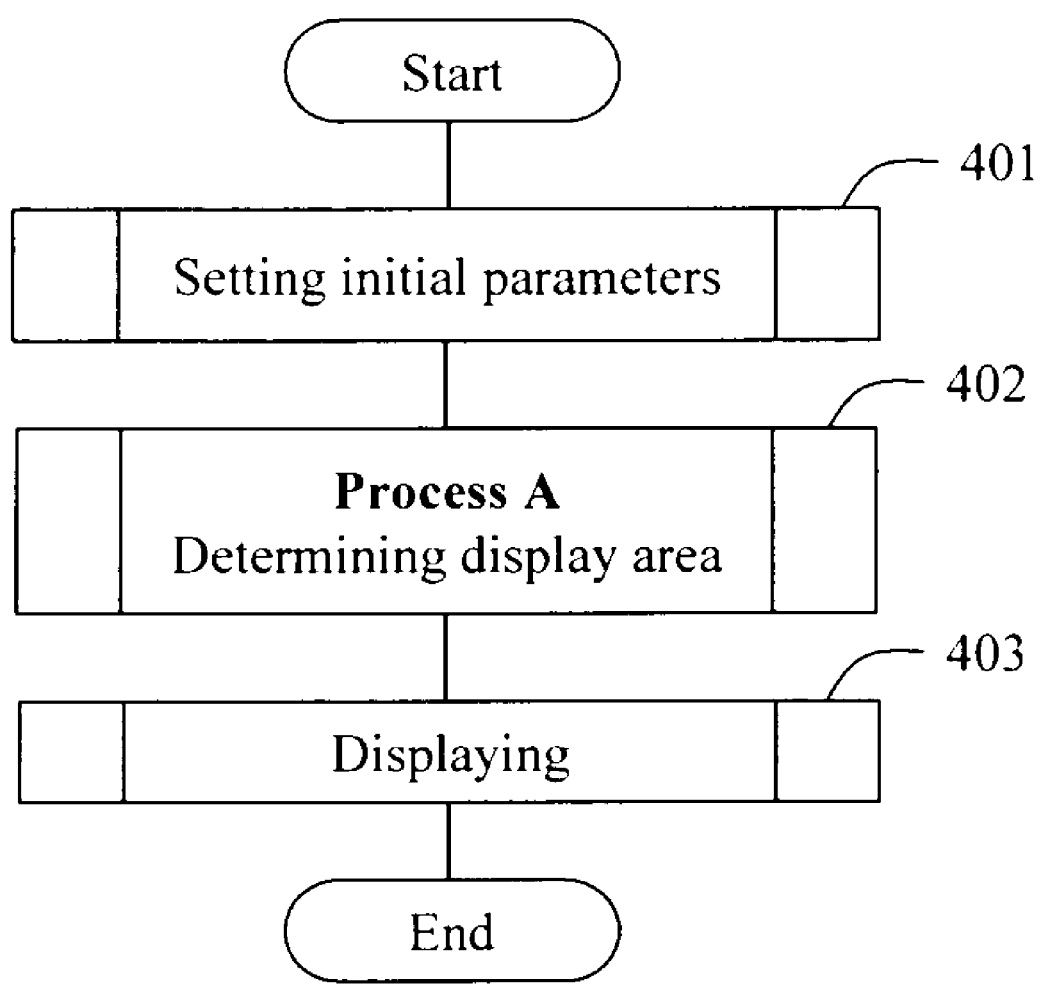
FIG. 4 is a flowchart showing a scheme of the clustering process.

FIG. 4 is a flowchart showing a scheme of algorithm employed in the clustering processor 105 for clustering and displaying gene expression pattern data.

First, initial parameters are set (Step 401) and a display area is determined (Step 402). The initial parameters will be described later in more detail. Then, displaying process is performed (Step 403), whereby the whole processing is ended. The present algorithm is for displaying expression patterns of different genes which at the beginning are the same but becomes different at some time point (FIG. 2).

Figure 5:
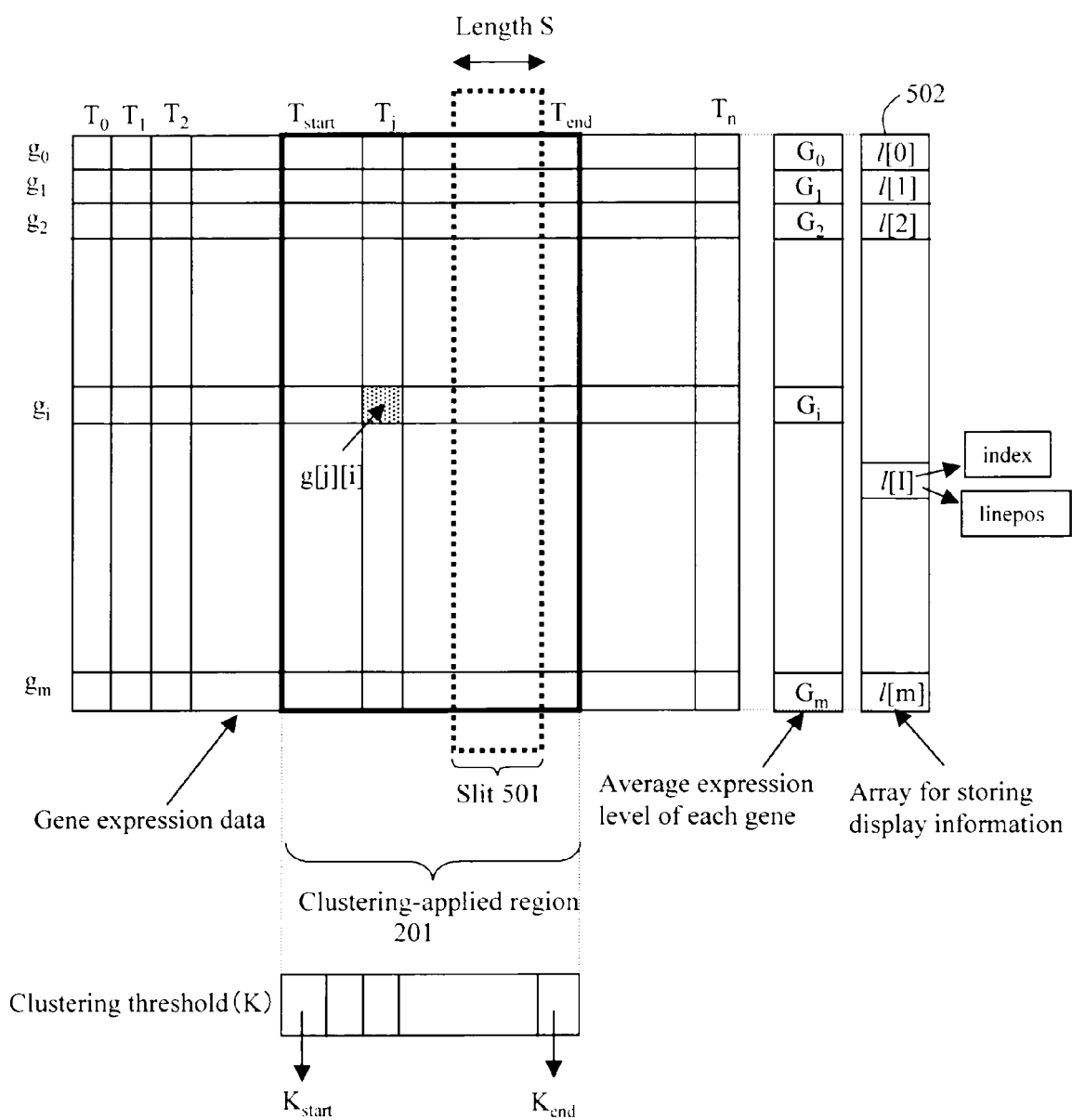
FIG. 5 is a diagram for illustrating the relationship between the variables used for clustering and the actual data.
Figure 6:
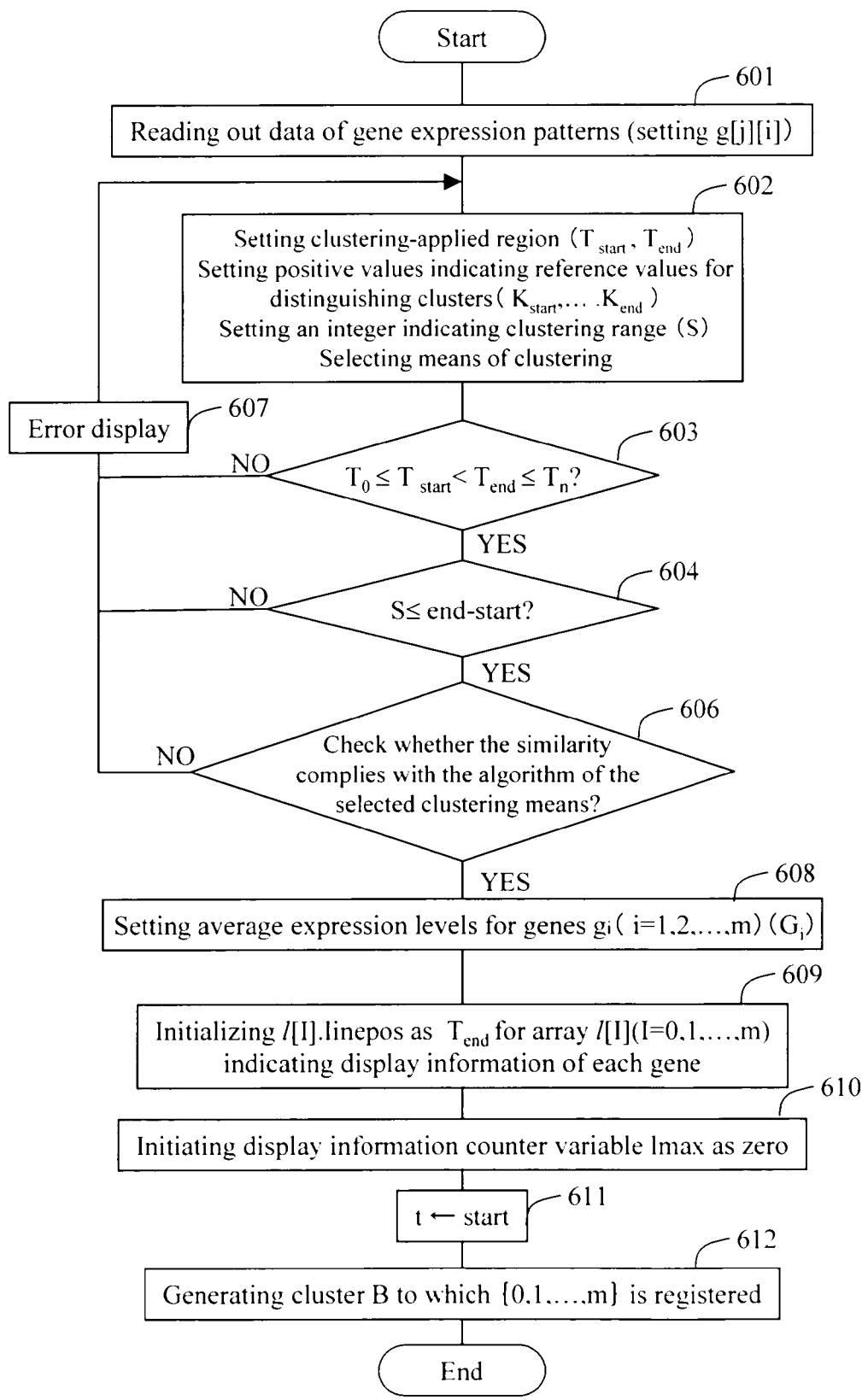
FIG. 6 is a flowchart showing an algorithm with respect to the process of setting the initial parameters.

FIG. 5 is an illustration showing the relationship between the variables used in the present algorithm and the actual data. FIG. 6 is a flowchart showing details of the algorithm with respect to the process of setting the initial parameters (Step 401 in FIG. 4).

First, data of gene expression patterns are read out from the storage medium 101. As shown in FIG. 5, the data of gene expression patterns contains expression pattern data of $m+1$ number of sample genes $g_0, g_1, \ldots g_m$, obtained by experiments at time $T_0, T_1, \ldots T_n$. The observed expression value of gene $g_j$ at time $T_i$ is indicated as $g[j][i]$ (Step 601).

Then, the keyboard 103 and the mouse 104 are used to input a clustering-applied region (starting time $T_{start}$ and ending time $T_{end}$), positive values ($K_{start}, K_{start+1}, \ldots K_{end}$) as reference values for distinguishing clusters, an integer (S) indicating a range of clustering, and the methods of clustering (Step 602).

Figure 24:
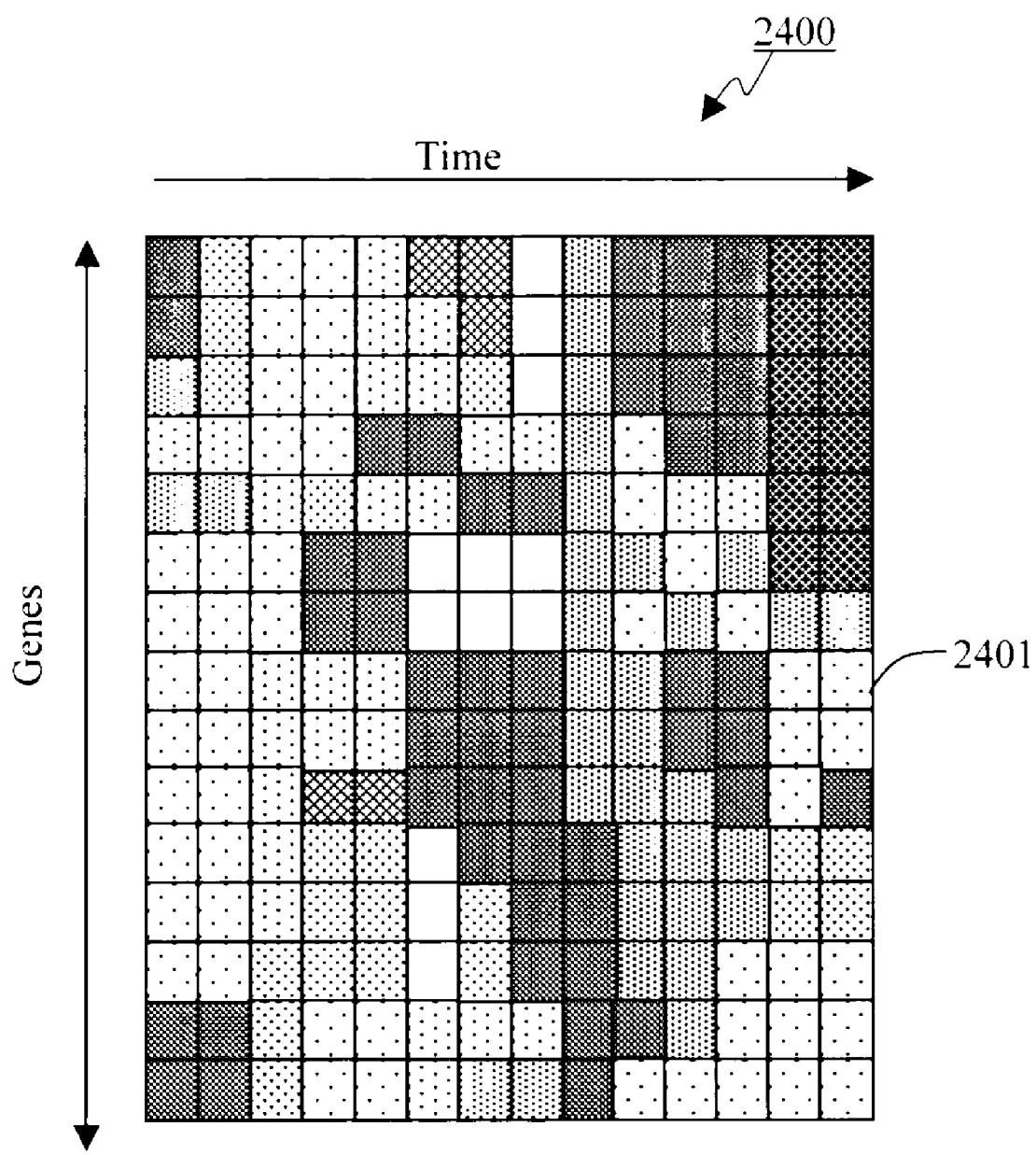
FIG. 24 is a diagram for illustrating an exemplary display of gene expression patterns obtained by clustering similar expression patterns together over the entire cell process.
Figure 25:
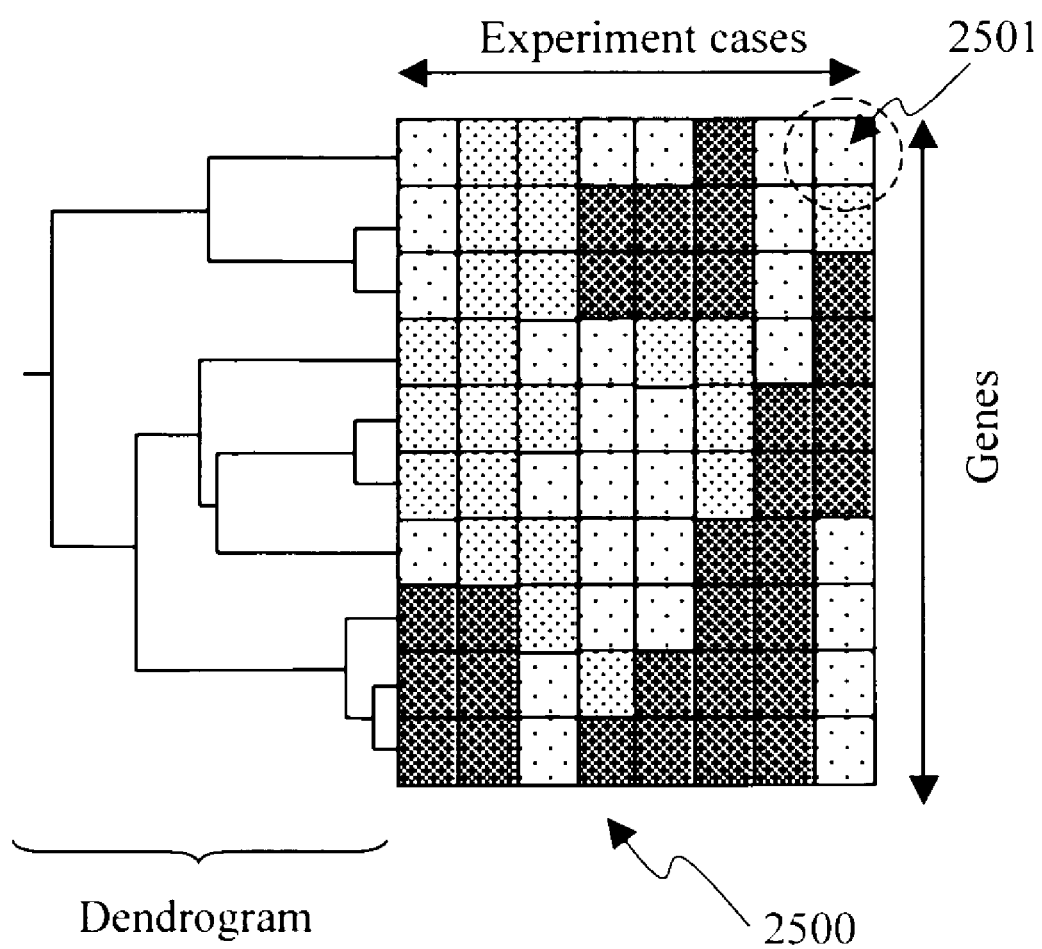
FIG. 25 is a diagram showing an exemplary display of the results of a standard clustering analysis of gene expression patterns.

The solid lines 201 in FIGS. 2 and 3 indicate the clustering-applied regions, namely a time segment within the cell cycle designated for further detailed clustering. For example, if a cell shows a particular expression pattern at some time point during the cell cycle, the clustering-applied region may be designated to include that time point to monitor in further detail the expression status of every gene. The present invention is different from the conventional clustering fundamentally in that it does not cluster genes with similar expression status over the entire cell cycle as shown in FIG. 24, but arranges the gene patterns such that different genes have the same expression patterns at the beginning of the region but become to have different expression patterns within the region as shown in FIG. 2.

The reference value for distinction between different clusters is a minimum value, namely threshold K, of dissimilarity between the clusters. Since thresholds can variably be set as $K_{start}, K_{start+1}, \ldots, K_{end}$, the level of clustering may be regulated to be brief or detailed along the time axis.

The present system does not target the entire expression data obtained at time $T_0, T_1, \ldots T_n$ for calculating dissimilarity for clustering, but selects a certain time segment to target data within that time segment for calculating dissimilarity. As shown in FIG. 5, this time segment is called a slit 501 and the length S (a width along the time axis) of this slit 501 is called a clustering range. According to the present algorithm, the beginning of the slit 501 is set to $T_{start}$ for clustering data within a range $T_{start}$ to $T_{start+S}$. Then, the slit 501 is shifted in a forward direction along the time axis to cluster each of the grouped clusters within a range $T_{start+1}$ to $T_{start+S+1}$. This procedure is repeated until the end of the slit reaches $T_{end}$. The smaller the clustering range is (i.e., the shorter the width of the time segment is), the more detailed difference between the gene expressions will be obtained.

In the clustering process, the similarity or dissimilarity which indicates correlation between the genes upon clustering (Pearson's correlation coefficient, squared Euclidean distance, standardized squared Euclidean distance, Mahalanobis' distance, Minkowsky distance, etc.) and algorithm for joining the clusters (nearest neighbor method, furthest neighbor method, group average method, centroid method, median method, Ward method, flexible method, etc.) are designated. The present algorithm utilizes dissimilarity. When similarity is selected for clustering, a minus sign may be applied in front of the calculated similarity to give an inverse number as for conversion to dissimilarity.

Once these values are set, each item is checked whether it is proper or not. The items are (i) whether the clustering-applied region $T_{start}$ to $T_{end}$ is included in the region $T_0$ to $T_n$ (Step 603), (ii) whether the clustering range S is within the width of the clustering-applied region (S≦end-start) (Step 604), and (iii) whether the similarity or dissimilarity complies with the algorithm of the selected clustering method (for example, when centroid method, median method or Ward method is employed as the algorithm, squared Euclidean distance should be selected) (Step 606). If any of these values is not proper, an error signal is output to the display device 102 to demand re-entering (Step 607).

When all of the set items are confirmed proper, an average level $G_i=(g[0][i]+g[1][i]+\ldots g[n][i])/n$ of expressions of a gene $g_i$ (where $i=1, 2, \ldots m$) is calculated (Step 608).

In order to store display information of each gene, an array l[I] (I=0, 1, ... m) 502 (FIG. 5) and an integer variable lmax are prepared. Each l[I] is a structure data that consists of a member indicating an index of a gene (index) and a member indicating the location of the dividing line between distinctive clusters (linepos) as shown in FIG. 5. The members of the structure can be set or referred to as l[I].index or l[I].linepos. For all "I", the value of l[I].linepos is initiated as $T_{end}$ (Step 609), and the value of lmax is set to "0" (Step 610). Then, the value of "start" is set to variable t (Step 611).

The present algorithm employs an abstract data type called "cluster" which indicates set of integers. A cluster has an interface for registration and deletion of an integer and for reference of the registered data.

Finally, cluster B is generated to which {0, 1, 2, ... m} is registered (Step 612), whereby the whole process is ended.

After the above-described initialization, the clustering-applied region 201 is processed. Specifically, the display area is determined by using t and B set above as arguments (Process A in Step 402 of FIG. 4).

Figure 7:
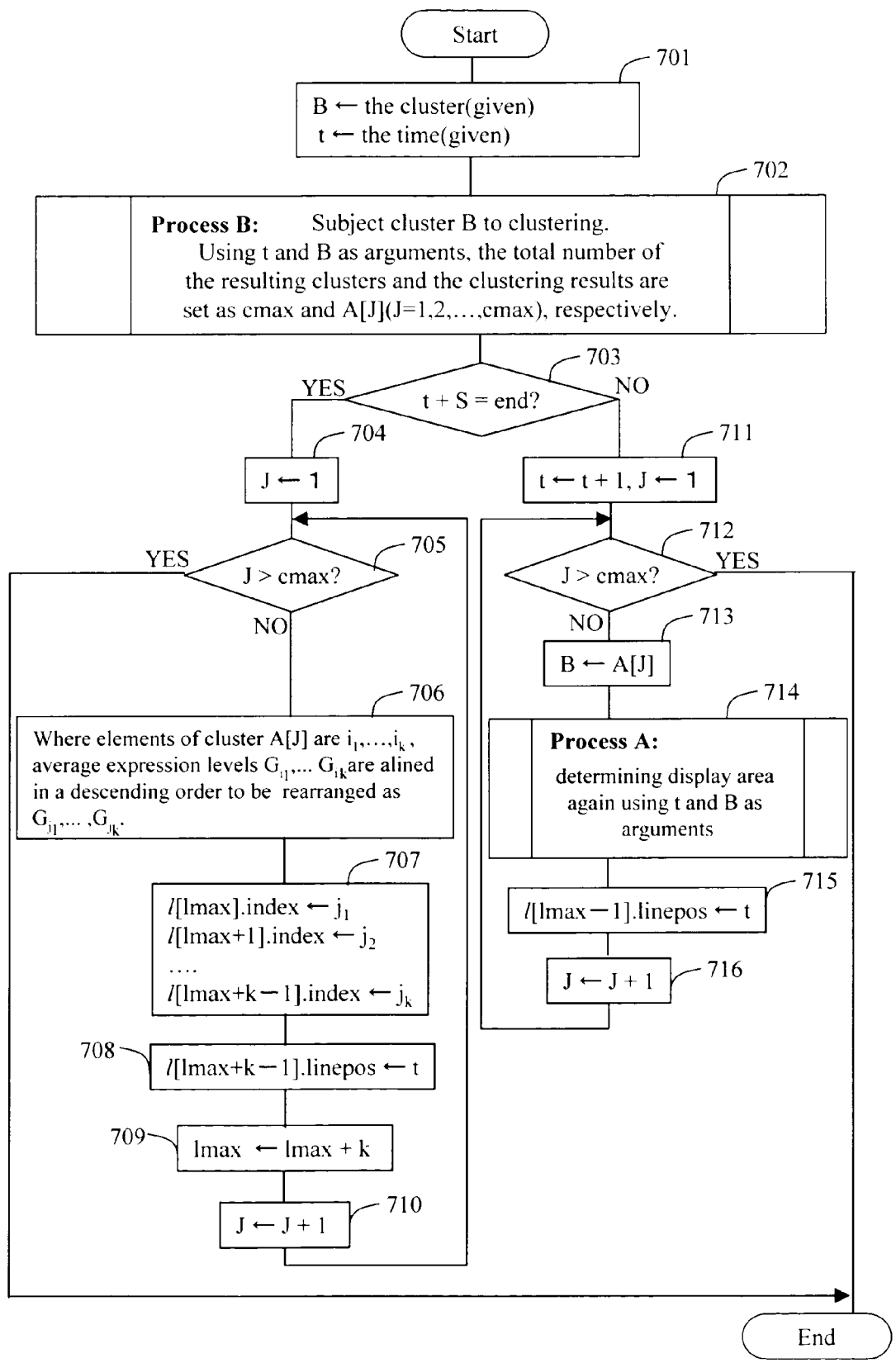
FIG. 7 is a flowchart showing an algorithm of the process of determining the display area.

FIG. 7 is a flowchart showing in detail the process of determining the display area (Process A) in FIG. 4. The display information is registered in the array l during this Process A.

First, let the given cluster and time be B and t, respectively, as arguments (Step 701). Then, B is subjected to clustering (Process B) where t and B are given as arguments. As a result of Process B, the total number of the clusters and the clustering results are set to cmax and A[J](J=1, 2, ... , cmax), respectively (Step 702). Details of Process B will be described later.

Then, whether "t+S" equals "end" is judged (Step 703). When they are equal, it means that the end of the slit 501 has reached the end of the clustering-applied region 201, whereby the clustering process is ended. The following process is executed for each cluster until J exceeds cmax (starting from J=1) (Steps 704 and 705). Where the elements of cluster A[J] are $\{i_1, \ldots, i_k\}$ these elements are aligned and displayed under a certain rule. Here, the average of the expression levels $G_{il}, \ldots G_{ik}$ corresponding to the elements are aligned in a descending order to be rearranged as $G_{jl}, \ldots G_{jk}$ (Step 706).

Then the value for array l is entered. Specifically, "l[ ].index" which indicates the positional information of the expression pattern data is set as l[lmax].index=$j_1$, l[lmax+1].index=$j_2$, ... , l [lmax+k−1].index=$j_k$ such that they are arranged in a descending order according to their average brightness (Step 707). The value "t" is entered into "l[lmax+k−1].linepos" which indicates the line for dividing distinctive clusters (a solid line 202 extending in horizontal direction is representatively shown in FIG. 2) from time "t" to "t+S (=$T_{end}$)" (Step 708).

Next, k is added to lmax for indicating the maximum number of the already entered data of array l (Step 709). Then, J is incremented to perform the next clustering (Step 710).

On the other hand, when "t+S" does not equal "end" (i.e., when the end of the slit 501 does not reach the end of the clustering-applied region 201) at Step 703, t is incremented and J is set to "1" (Step 711). The following procedure is performed for each cluster until J exceeds cmax (Step 712). Specifically, A[J] is substituted for B (Step 713), and the display area is determined using time t and cluster B as arguments (Process A) (Step 714). Then, the value "t" is entered into "l[lmax−1].linepos" which indicates a line for dividing distinctive clusters from time "t" to "$T_{end}$" (Step 715). Then, J is incremented to perform the next clustering (Step 716). If the procedure is finished for all clusters A[J] (J=1, ... , cmax), the process is ended.

Figure 8:
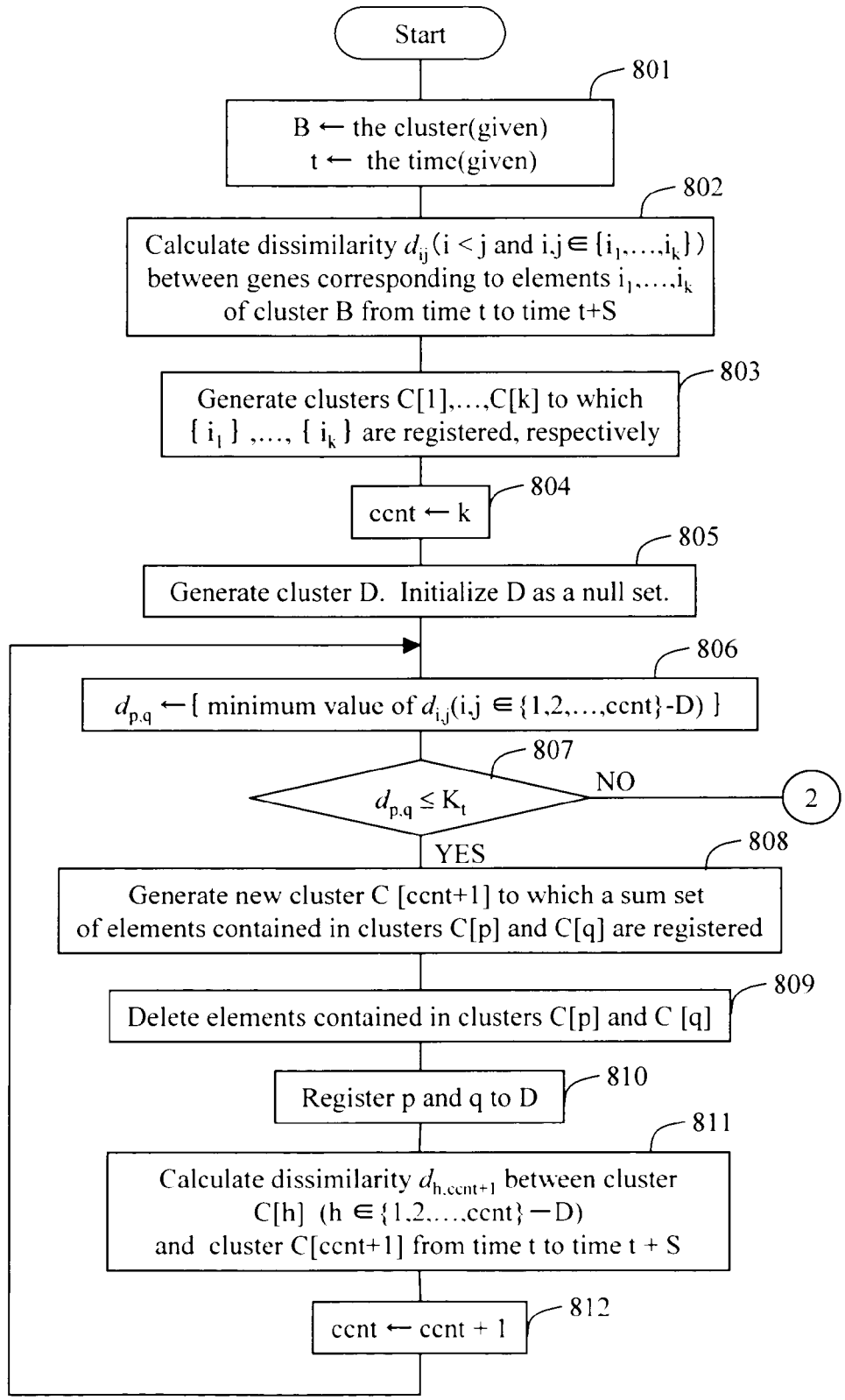
FIG. 8 is a flowchart showing an algorithm for clustering.
Figure 9:
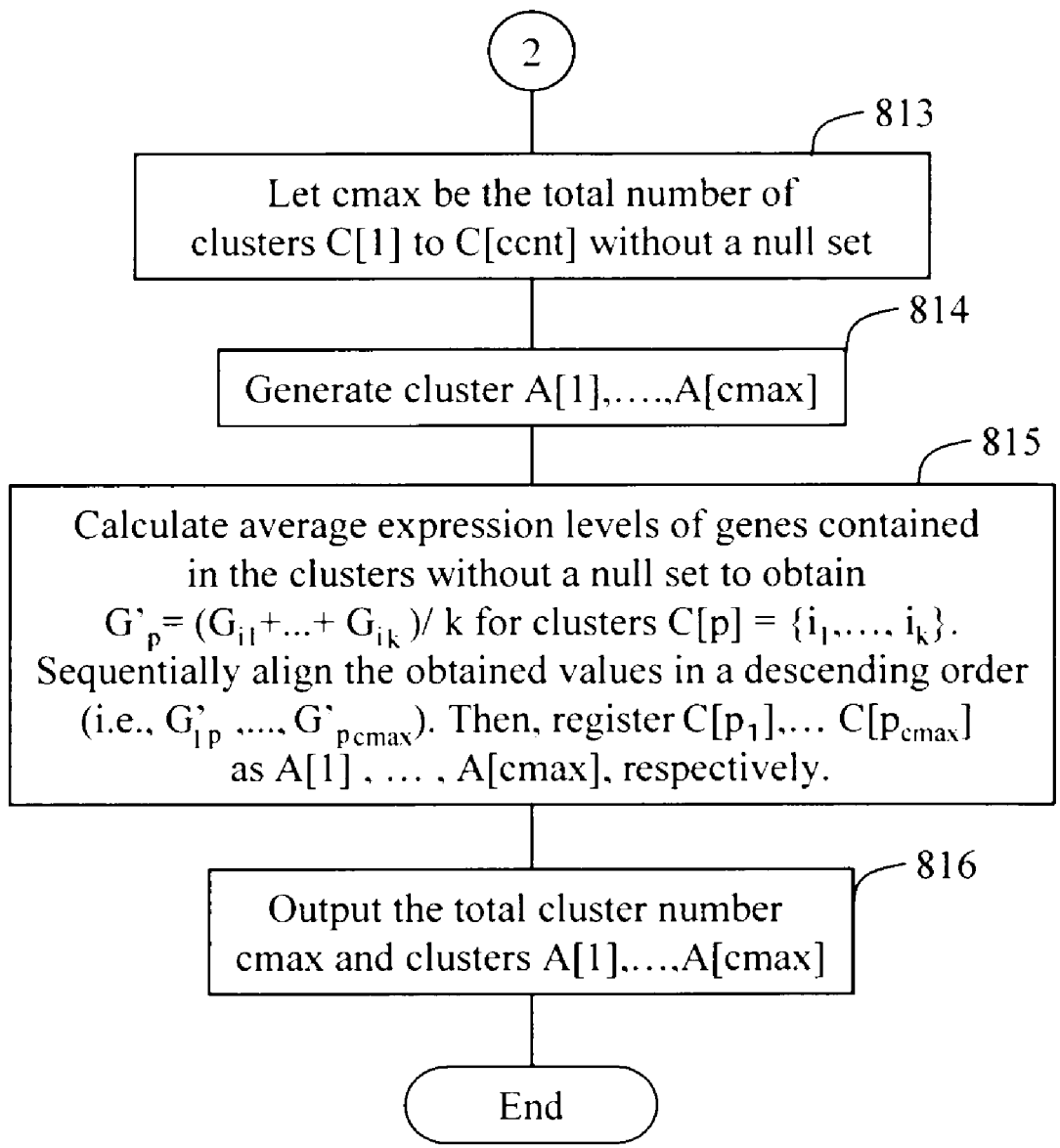
FIG. 9 is a flowchart showing the process following the process shown in FIG. 8.

FIGS. 8 and 9 are flowcharts showing algorithm of the clustering process (Process B).

First, the entered cluster and time are used as arguments B and t, respectively (Step 801).

Then, where the elements of cluster B are $i_1, \ldots, i_k$, similarity or dissimilarity $d_{ij}$ (i<j and i,j∈$\{i_1, i_2, \ldots, i_k\}$) between genes corresponding to $i_1, \ldots, i_k$ from time t to time t+S is calculated (Step 802).

The similarity (dissimilarity) of gene expression data {g [0] [i], g [1] [i], ... , g [n] [i]} of genes $g_i$, $g_j$ is a value obtained, for example, by the following calculation (Step 802).

(1) When Pearson's correlation coefficient is designated as similarity, $$d_{i,j} = \frac{\sum_{k=t}^{t+S}(g[k][i] - \overline{g[i]})(g[k][j] - \overline{g[j]})}{\sqrt{\left\{\sum_{k=t}^{t+S}(g[k][i] - \overline{g[i]})^2\right\}\left\{\sum_{k=t}^{t+S}(g[k][j] - \overline{g[j]})^2\right\}}} \quad \text{where} \quad (1)$$

$$\overline{g[l]} = \frac{1}{S}\sum_{k=t}^{t+S} g[k][l]$$

Since the present algorithm targets dissimilarity, the obtained similarity has to be converted to dissimilarity by providing with a minus sign to give an inverse number.

(2) When squared Euclidean distance is designated as dissimilarity, $$d_{i,j} = \sum_{k=t}^{t+S} (g[k][i] - g[k][j])^2 \quad (2)$$

(3) When standardized squared Euclidean distance is designated, $$d_{i,j} = \sum_{k=t}^{t+S} (g[k][i] - g[k][j])^2 / s_k^2 \quad (3)$$

where $S_k^2$ is a variance of variable g[k] [0], . . . , g[k] [n]

(4) When Mahalanobis' distance is designated, $$d_{i,j} = {}^t(g[i] - g[j])S^{-1}(g[i] - g[j]) \quad (4)$$

where g [l]=$^t$(g [t] [l], . . . , g [t+S] [l]), and S is covariance matrix of g[i], g[j].

(5) When Minkowsky distance is designated, $$d_{i,j} = \left\{ \sum_{l=t}^{t+S} |g[l][i] - g[l][j]|^k \right\}^{1/k} \quad (5)$$

Then, clusters C[1], . . . , C[k] are generated which are registered as C[1]←{i$_1$}, . . . , C[k]←{i$_2$} (Step 803) Variable ccnt indicating the number of the generated clusters is substituted with k (Step 804). Then, a null set of cluster D is generated (Step 805).

Then the minimum value $d_{p,q}$ of the calculated dissimilarity $d_{i,j}$ (i,j∈{1, 2, . . . , ccnt}-D) is obtained to judge whether it is less than the preset threshold $K_t$ (Steps 806 and 807). When $d_{p,q}$ is less than $K_t$, the following procedure takes place. Cluster C[ccnt+1] is newly generated. A sum set of elements contained in clusters C[p] and C[q] is registered into cluster C[ccnt+1] (Step 808) and the elements are deleted (Step 809). Since C[p] and C[q] are no longer necessary, p,q are registered into D (Step 810). Then, dissimilarity $d_{h,ccnt+1}$ between cluster C[h] (h ∈{1, 2, . . . , ccnt}-D) and cluster C[ccnt+1] from time t to time t+S is obtained (Step 811). $d_{h,ccnt+1}$ can be obtained by the following calculation, where when n(k) is the number of elements in cluster C[k] and:

(1) when the clustering method is nearest neighbor method, α

$$d_{h,ccnt+1} = \alpha d_{h,p} + \beta d_{h,q} + \gamma d_{p,q} + \epsilon |d_{h,p} - d_{h,q}| = 0.5, \beta = 0.5, \gamma = 0 \text{ and } \delta = -0.5; \quad (6)$$

(2) when the clustering method is furthest neighbor method, α=0.5, β=0.5, γ=0 and δ=0.5;
(3) when the clustering method is group average method, α=n(p)/n(ccnt+1), β=n(q)/n(ccnt+1), γ=0 and δ=0;
(4) when the clustering method is centroid point, α=n(p)/n(ccnt+1), β=n(q)/n(ccnt+1), γ=−n(p)$_n$(q)/n(ccnt+1)$^2$, and δ=0;
(5) when the clustering method is median method, α=0.5, β=0.5, γ=−0.25 and δ=0; or
(6) when the clustering method is Ward method, α={n(h)+n(p)}/{n(h)+n(ccnt+1)}, β={n(h)+n(q)}/{n(h)+n(ccnt+1)}, γ=−n(h)/{n(h)+n(ccnt+1)} and δ=0.

Then, "1" is added to the variable ccnt indicating the number of the generated clusters (Step 812). The above-described procedure is repeated until the minimum value of updated dij (i,j∈{1, 2, . . . ccnt}-D) exceeds $K_t$.

When the minimum value $d_{p,q}$ of $d_{i,j}$ exceeds $K_t$ at Step 807, clustering is finished and the results are output. First, clusters which do not contain a null set are judged and determined among clusters C[1] to C[ccnt] and the total number thereof is entered as cmax (Step 813). Then, cmax number of clusters A[1], . . . , A[cmax] are generated (Step 814). Average expression levels of genes contained in the clusters without a null set are calculated, that is, to obtain G'$_p$=(G$_{i1}$+ . . . +G$_{i,k}$)/k for clusters C[p]=i$_1$, . . . , i$_l$. Where the obtained values sequentially aligned in a descending order are G'$_{p1}$, . . . G'$_{pcma}$, A[1], . . . A[cmax] are registered as C[p$_1$], . . . C[p$_{cmax}$] (Step 815). Finally, the total cluster number cmax and clusters A[1], . . . , A[cmax] are output (Step 816), thereby ending the whole process.

Figure 10:
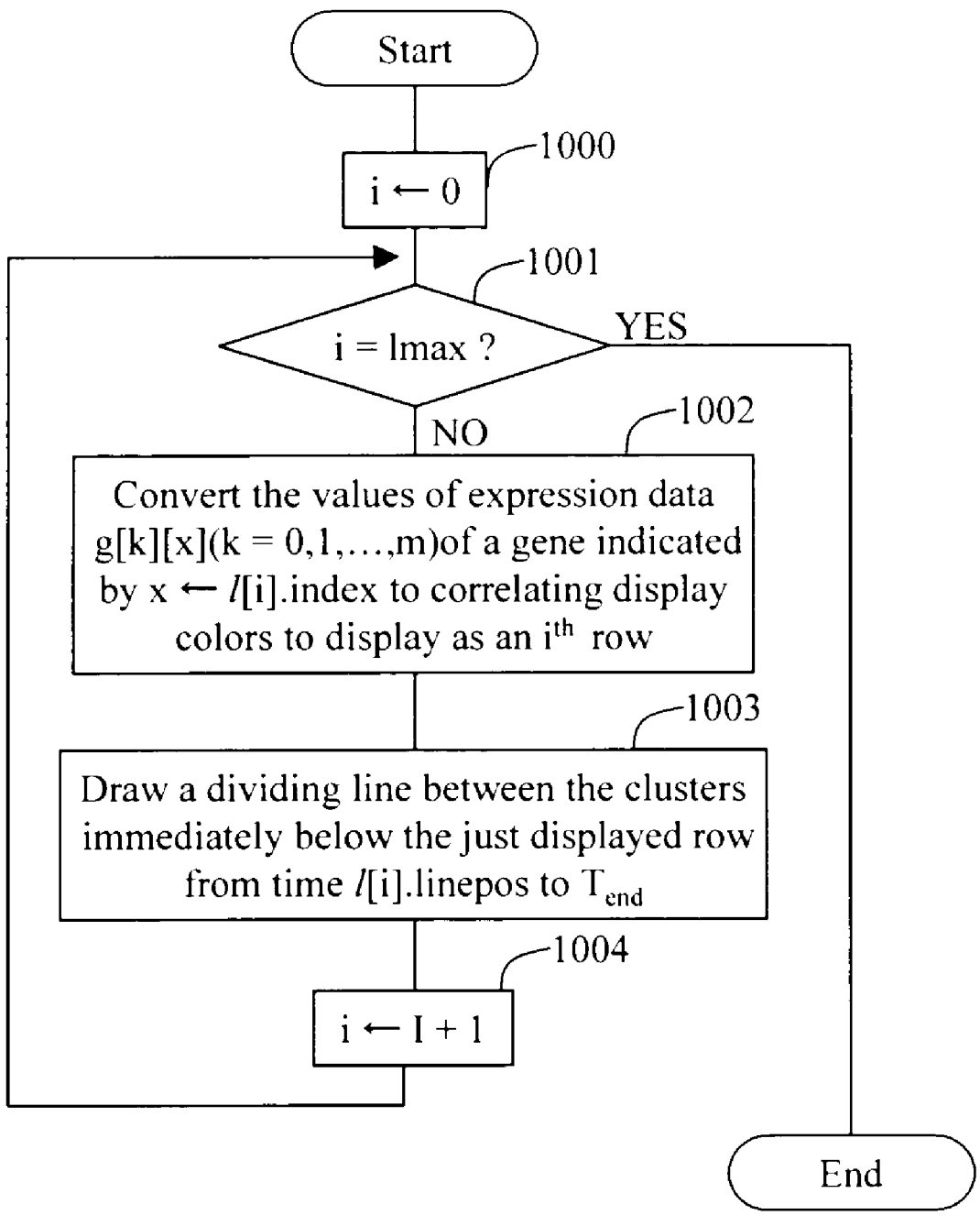
FIG. 10 is a flowchart showing a general algorithm for displaying.

FIG. 10 is a flowchart showing detailed algorithm of the displaying process shown in FIG. 4. This algorithm reads out array l[I] and displays expression data of a corresponding gene.

First, let value i be "0" (Step 1000) and repeat the following procedure for each gene expression data until value i equals lmax (Step 1001). Then, the values of expression data g[k] [x] (k=0, 1, . . . , n) corresponding to a single row of a gene indicated by x=l[i].index is converted to correlating display colors to be displayed as an i$^{th}$ row (Step 1002). The dividing line between the clusters is drawn immediately below the just displayed i$^{th}$ row from time [i].linepos to T$_{end}$ (Step 1003).

Where l[i].linepos is initial value T$_{end}$, there is no need of drawing a dividing line between the clusters. i is incremented for 1 (Step 1004) and the entire procedure is ended when i becomes lmax at Step 1001.

By the above-described process, expression patterns of different genes can effectively be displayed such that the patterns are arranged to be the same at the beginning of the clustering- applied region and become different at some time point in the region, as shown in FIG. 2.

On the other hand, gene expression patterns of different genes can effectively be displayed such that the patterns are arranged to be different at the beginning of a clustering-applied region and become the same at some time point in the region, as shown in FIG. 3. Such display can be realized by setting l[i].linepos to T$_{start}$ at Step 609 (FIG. 6), setting t to end at Step 611, setting the judgment condition t+S=end to t-S=start at Step 703 (FIG. 7), substituting t←t−1 for t←t+1 at Step 711, and drawing a dividing line between clusters within a range T$_{start}$ to l[i].linepos. This means that the end of a slit is set to T$_{end}$ at the beginning and then clustering step is performed while shifting the slit in a reverse direction along the time axis.

Figure 11:
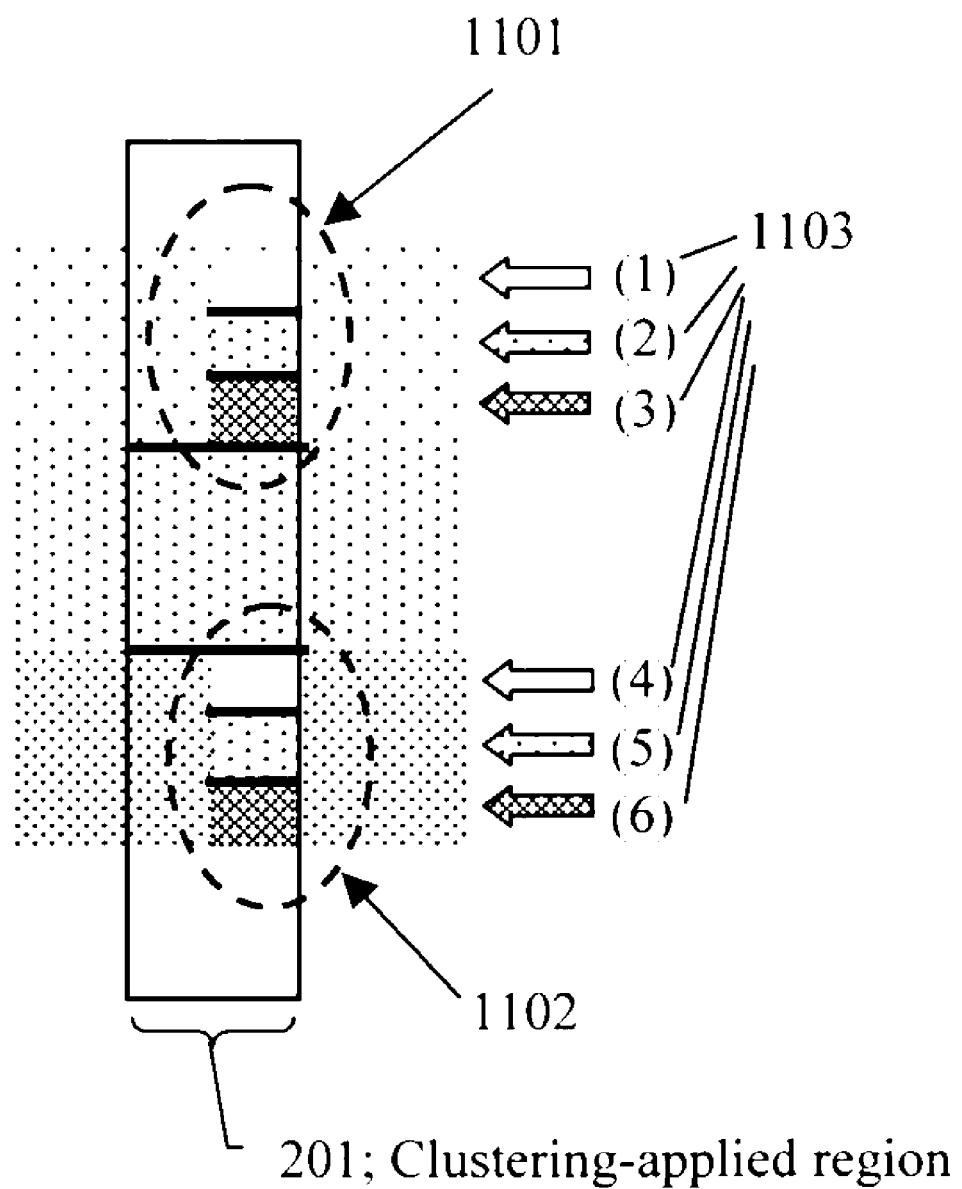
FIG. 11 is a diagram for illustrating an exemplary display of gene expression patterns resulting from clustering carried out by shifting a slit from the beginning of the clustering-applied region in a forward direction along the time axis.
Figure 12:
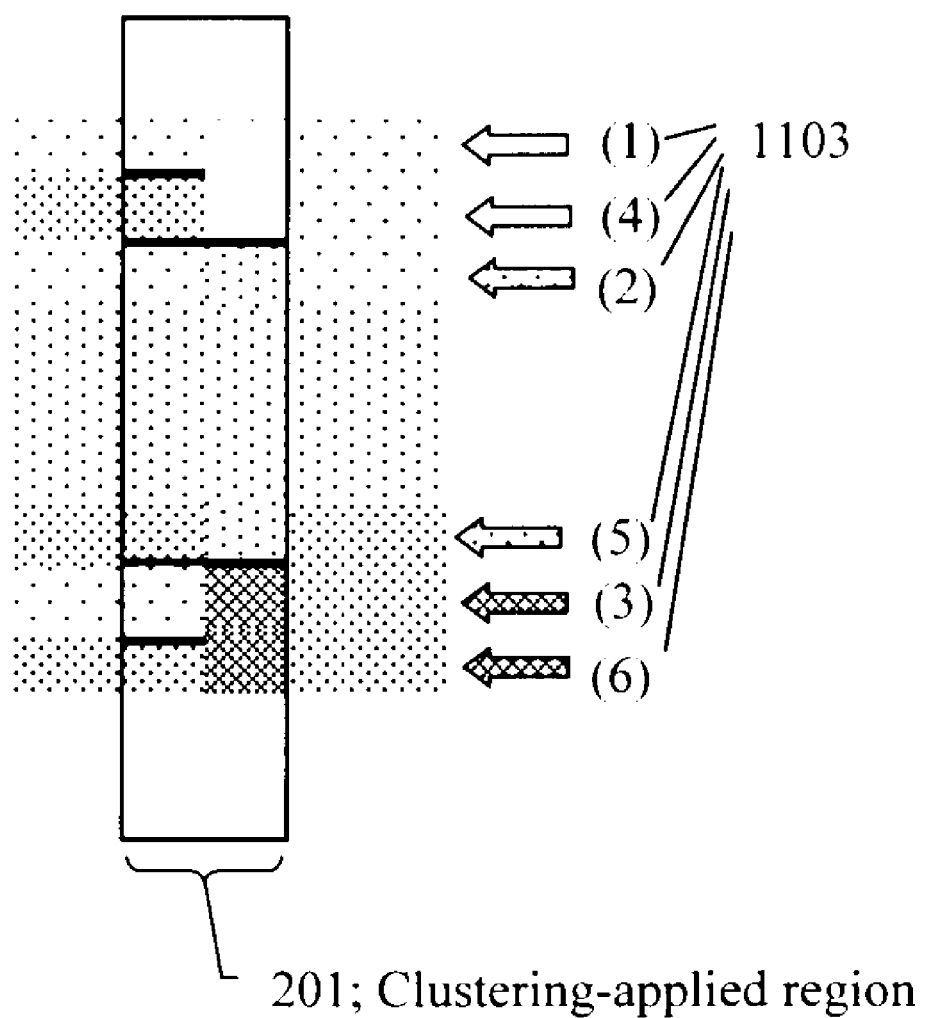
FIG. 12 is a diagram for illustrating an exemplary display of gene expression patterns resulting from clustering carried out by shifting a slit from the end of the clustering-applied region in a reverse direction along the time axis.

Hereinafter, an exemplary application of such clustering method will be described, where clustering is performed by shifting the slit from the beginning of the clustering-applied region in a forward direction along the time axis to give a display shown in FIG. 11. When expression patterns resembling each other (enclosed with dotted lines 1101 and 1102 in FIG. 11) are obtained, these genes are marked (1103) and clustering is performed for them from the end of the clustering-applied region 201 in the reverse direction along the time axis. If the marked genes (1103) are at close locations as shown in FIG. 12 (e.g., (1) and (4), (3) and (6)), these genes should have different expression patterns at the beginning and should become to have the same expression patterns at some point. Such bi-directional clustering allows easy guessing of expression status of each gene.

Furthermore, where $T_{start}$, $T_{end}$ and slit width S are set to $T_0$, $T_n$ and n, respectively, the same display as that of the result of P. Brown et al. mentioned in the Background of the Invention can be obtained.

The present example is not limited to the above description, and details can be modified upon practice. For example, the boundary where the expression pattern changes can be displayed with a combination of known display formats, such as a flicker display, a bright display and a color reversion display.

The processing by the clustering processor 105 can be stored as a program in a storage medium (e.g., CD-ROM) to be provided to a user of a computer.

The data of genes is not limited to time sequential expression data, and the horizontal axis (time axis) shown in FIGS. 2 and 3 may represent other basis. For example, expression patterns of cancerous and normal cells from the same human tissue can be combined and simultaneously clustered so as to find genes that specifically function to cancer, genes that specifically function to normal cells and genes that specifically function to both types of cells.

Figure 23:
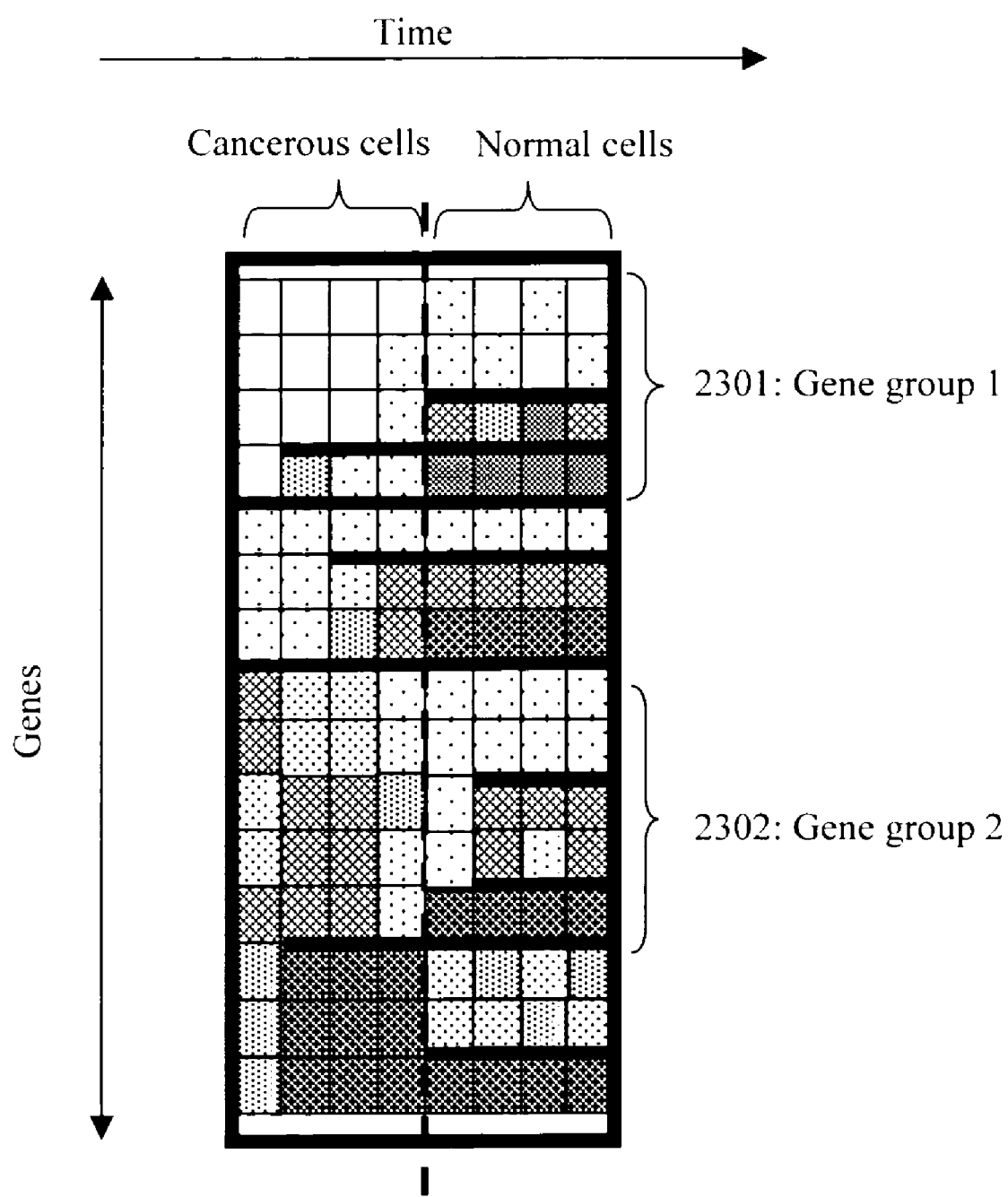
FIG. 23 is a view showing an example of combining and clustering cancerous and normal cells.

FIG. 23 is a view showing an example of combining and clustering cancerous and normal cells according to the present embodiment. Referring to a gene group 1 (2301) in FIG. 23, genes as a whole are strongly expressed in the cancerous cells while some of the genes are expressed but some are not in the normal cells. Referring to other gene group 2 (2302), while weakly expressed genes are gathered in the cancerous cells, some of the genes are expressed but some are not in the normal cells. By simultaneously clustering two types of cells as described above, the behaviors of genes can generally be understood in detail.

Other than comparing difference between states at different time points or between states of tissues, comparison can be made for difference between species such as human and yeast, difference between sites of individual such as stomach, large intestine and heart, difference of expression patterns obtained upon electric shock, shock by high temperature or shock by low temperature, difference between presence and absence of an artificial condition, for example, expression patterns before and after drug administration, or difference of a combination thereof.

Hereinafter, another embodiment of the invention will be described.

Figure 13:
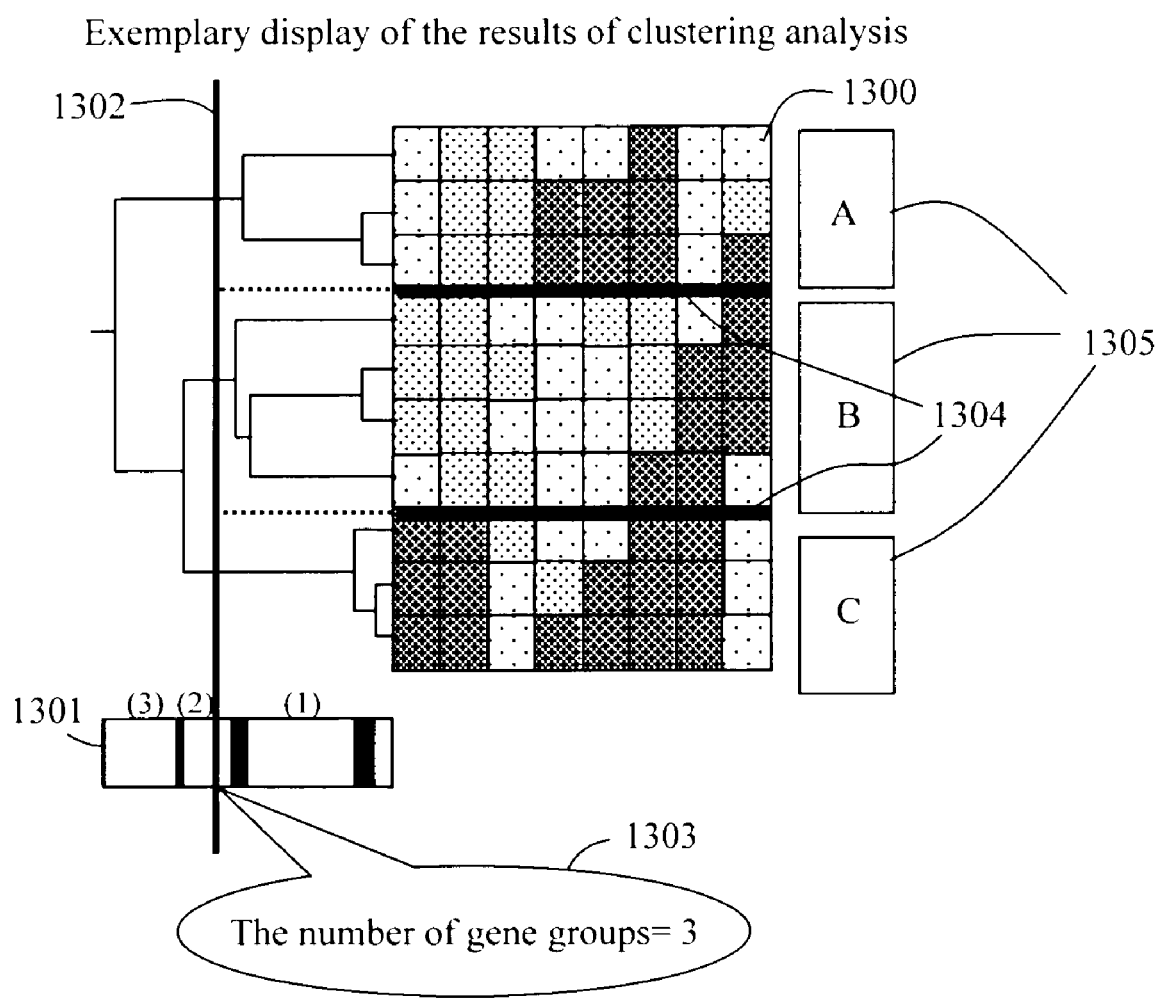
FIG. 13 is a schematic view showing an exemplary display of the results of a clustering analysis of gene expression patterns according to the present invention.

FIG. 13 shows an exemplary display of results of a clustering analysis according to the present invention.

Figure 26:
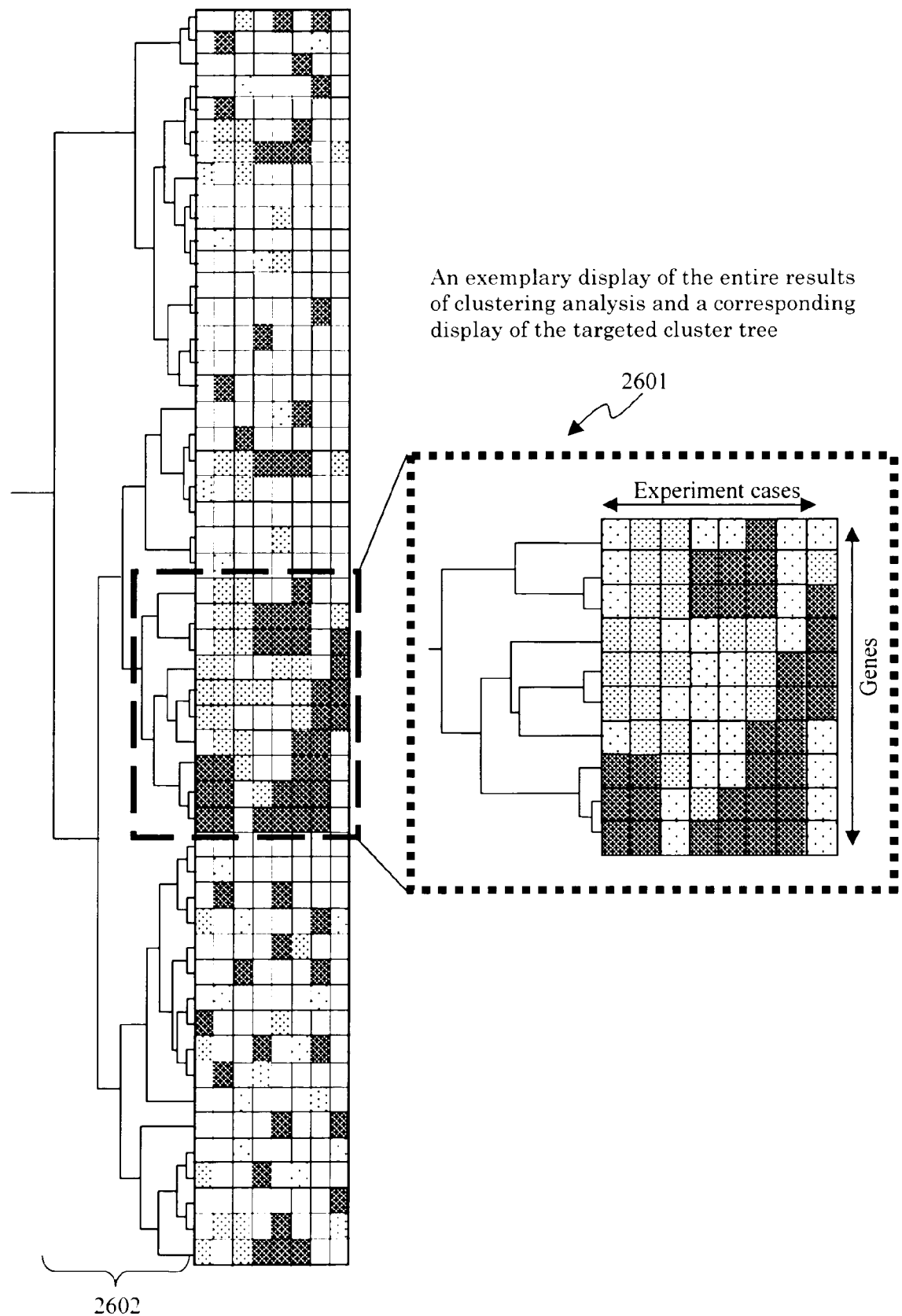
FIG. 26 is a schematic diagram showing an exemplary display of the entire results of clustering analysis and a corresponding display of the targeted cluster tree.

The display shown in FIG. 13 is based on a part of the left part corresponding to the part surrounded by a dotted line 2601 on the right part of FIG. 26, the left part showing the entire results of clustering a mass amount of gene expression pattern data. However, FIG. 13 may represent the entire results of clustering shown on the left part in FIG. 26.

In FIG. 13, a dendrogram cross-cutting line 1302 movable on a phase scale bar 1301 can be controlled by a user with a pointing apparatus such as the mouse 104 to find out the expression status at a second section ((2)) of the phase scale bar 1301. It indicates information 1303 (a round number of clusters) that three gene groups exist at the second section as a result of the clustering.

A dividing line 1304 is drawn on the gene expression pattern data 1300 and the resulting gene groups A, B and C are specified (by a gene group-specifying marks 1305).

FIG. 14 shows a specific structure of the gene expression pattern data 100 stored in the storage memory 101. The gene expression pattern data 100 exemplified here has m number of vector data 1402 corresponding to the number of gene IDs 1401. The indices of the arrays correspond to n number of experiment cases. Each element of the arrays stores numerated data of gene expression levels (brightness of the hybridized fluorescent signals).

Figure 15:
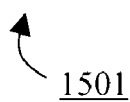
FIG. 15 is a schematic diagram showing an exemplary structure of a cluster.
Figure 15:
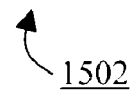

FIG. 15 shows exemplary cluster structures utilized upon clustering. There are two types of cluster structures, namely a cluster structure 1501 whose type member value is "leaf" (left) and a cluster structure 1502 whose type member value is "node" (right).

The leaf-type cluster structure 1501 corresponds to expression pattern data of each gene (i.e., each array data of FIG. 14), and the gene ID indicates a value of the gene ID member (e.g., 17). The "level" of the cluster is set to zero.

The node-type cluster structure 1502 is sequentially generated upon the joining process during clustering. The two clusters prior to joining can be reached based on the values of the left member and the right member, and the distance therebetween is stored as a value of the distance member. The level of the cluster is set considering a value of a recognition error range (e.g., 5).

Figure 16:
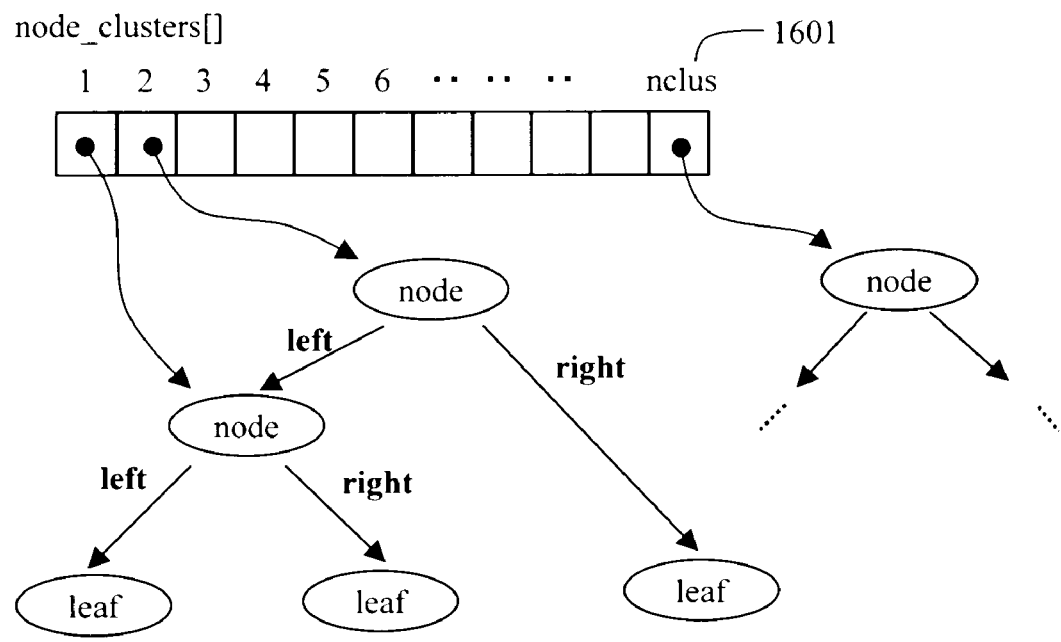
FIG. 16 is a schematic diagram showing an example of generating a tree structure of clusters.

FIG. 16 is a diagram showing a structure of data generated during the course of clustering analysis. At the beginning, there are only the leaf-type cluster structures 1501. Then, every time the structures 1501 are paired during the course of clustering analysis, a node-type cluster structure 1502 is generated, thereby configuring a tree-structure. The node-type cluster structures 1502 are linked in the order of generation so that it can be reached from the array node_clusters[ ]. Variable nclus 1601 gives the total number of the generated node-type cluster structures 1502.

Figure 17:
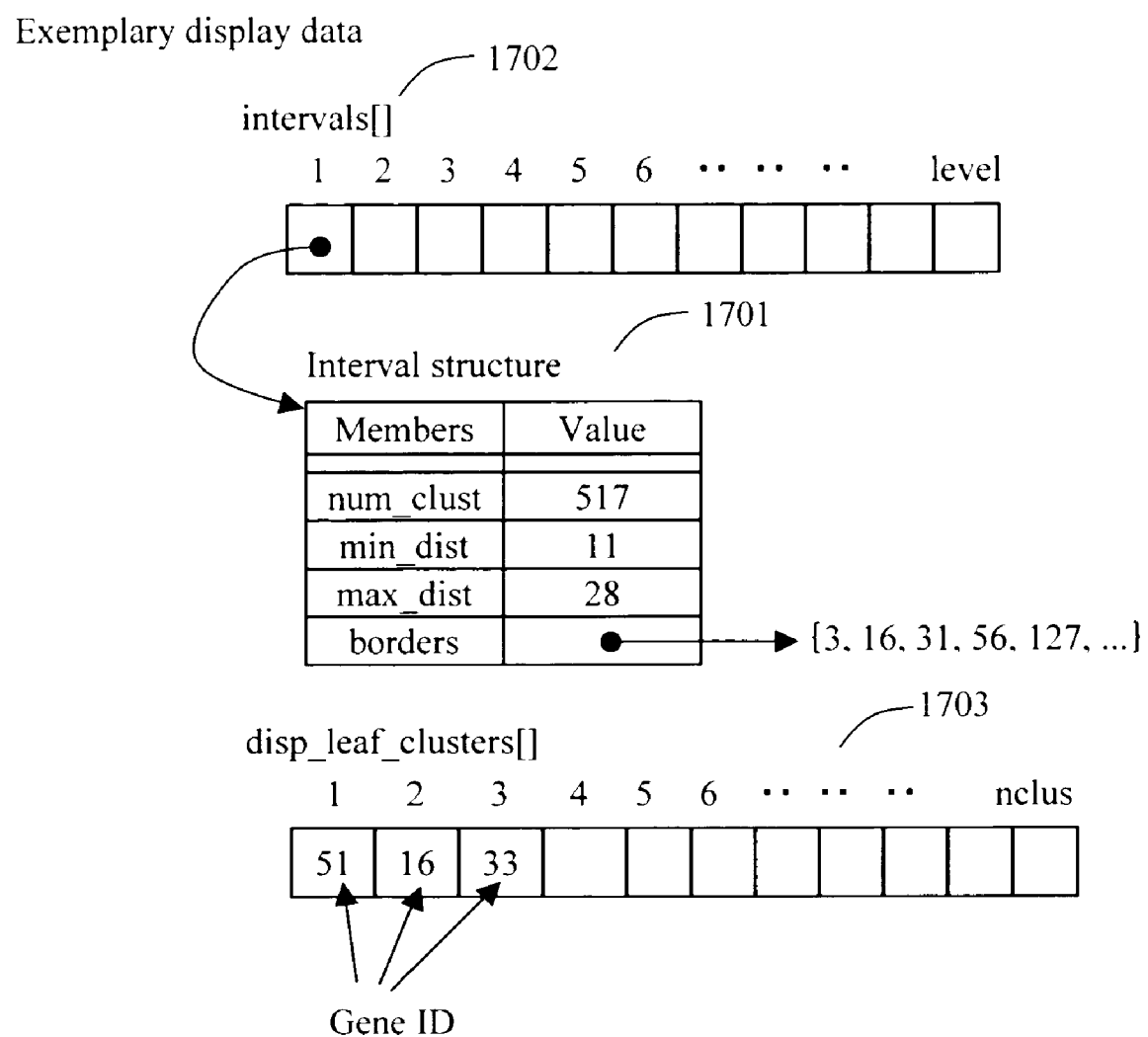
FIG. 17 is a diagram showing an example of display data.

FIG. 17 is a diagram showing an example of a data structure for storing the number of gene groups resulting from a certain analysis and display information for drawing the dividing line 1304 between the gene groups. The interval structures 1701 corresponding to the phase of the phase scale bar 1301 are sequentially generated during the grouping process considering the recognition error range, and are linked so that they can be reached from the array intervals[ ] 1702. The variable level stores the total number of the generated interval structures.

Each interval structure 1701 has members such as num_clust, min_dist, max_dist and borders. The num_clust member has information of the number of the gene groups upon grouping, min_dist and max_dist members have the minimum and maximum values, respectively, in the phase with respect to the distance between the clusters, and the borders member has the positional information (the line number) for drawing a dividing line in the gene expression pattern data 1300.

In order to determine which vector data corresponding to the gene ID (FIG. 14) should be displayed on which line of the gene expression pattern data 1300, the array disp_leaf_clusters[ ] 1703 is provided with the gene ID value to be displayed as $i^{th}$ array element corresponding to $i^{th}$ line.

Figure 18:
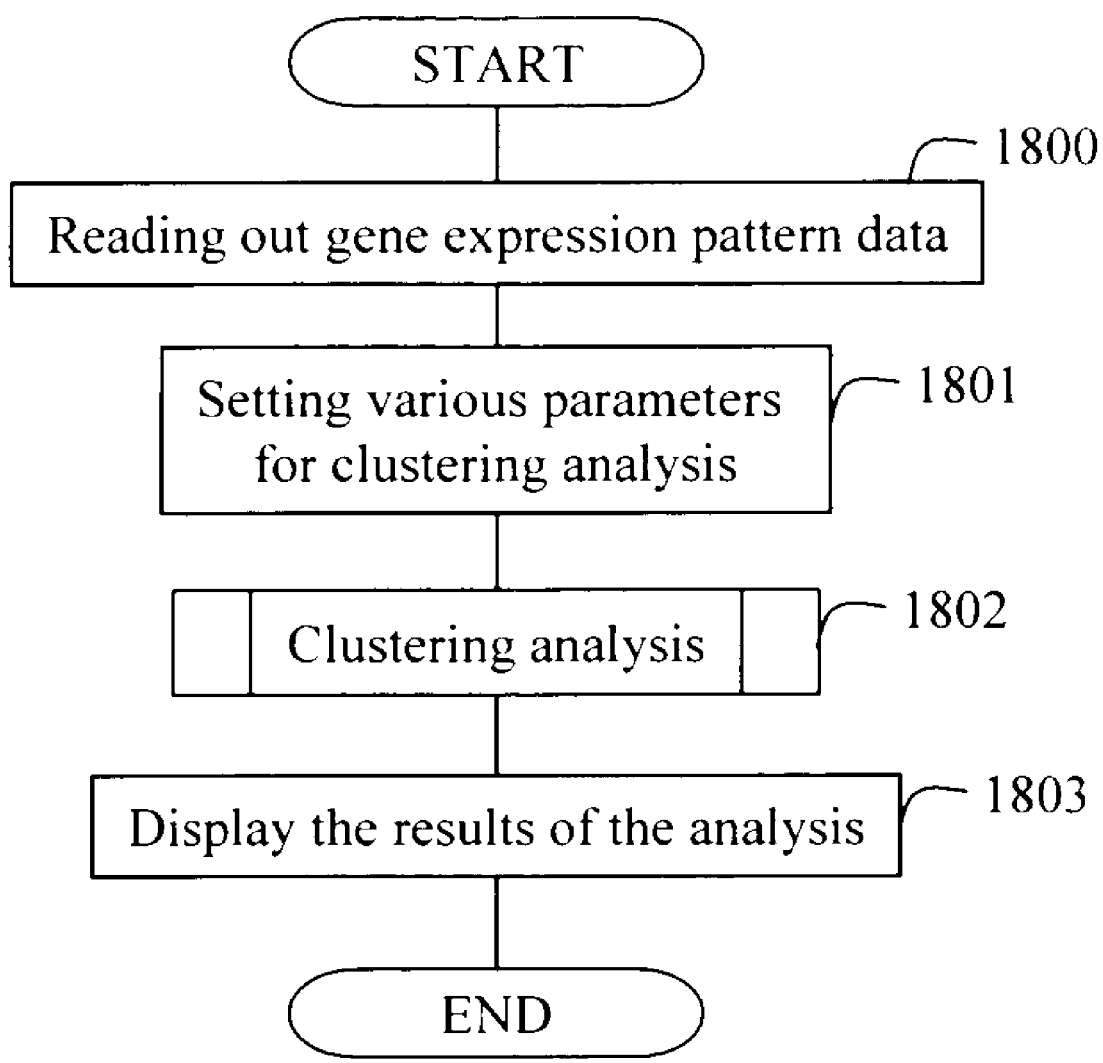
FIG. 18 is a flowchart showing a general process of displaying gene expression patterns according to the invention.

FIG. 18 is a flowchart showing a general process according to a method for displaying gene expression patterns of the present embodiment.

First, the gene expression pattern data 100 stored in the storage medium 101 is read by the display processor 105 (Step 1800). The specific structure of the expression pattern data 100 is shown in FIG. 14.

Next, each of the parameters necessary for the clustering analysis is set (Step 1801). At this point, the recognition error range entered by the user with the keyboard 103 is accepted and stored as variable E. The recognition error range provides a threshold for defining dissimilarity or similarity between expression pattern data of two genes shown in FIG. 14. Specifically, when the difference between the expression patterns is greater than the recognition error range, they are distinguished as distinctive data.

After setting the parameters, clustering analysis is performed (Step 1802). During this clustering analysis, information necessary for the display according to this embodiment is collected and display data is calculated, which will be described later in detail.

Finally, the results of the analysis are displayed (Step 1803). The previously collected and calculated display data are used for the characteristic display of the present embodiment (i.e., the phase scale bar 1301, the dendrogram cross-cutting line 1302, the dividing line 1304 of the gene expression pattern data, and the gene-group-specifying marks 1305).

It is also possible to display the gene-group-specifying marks 1305 only for clusters consisting of at least a predetermined number of gene expression data, and not to display for clusters consisting of data less than the predetermined number of gene expression data.

Figure 19:
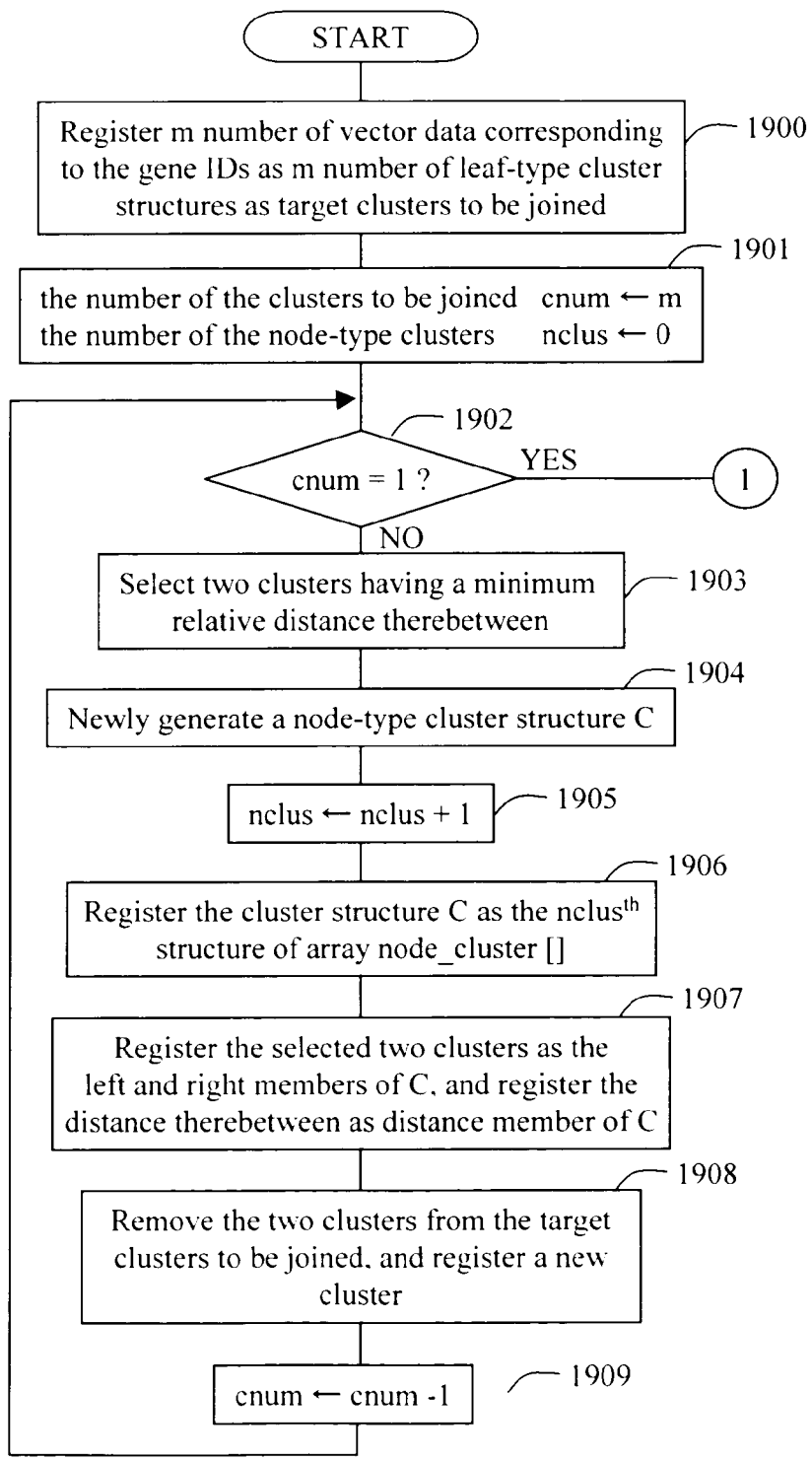
FIG. 19 is a flowchart for illustrating clustering analysis with respect to the process of generating a cluster tree.

FIG. 19 is a flowchart showing the process of clustering analysis (Step 1802) shown in FIG. 18 in detail with respect to the process of generating a cluster tree (the first-stage execution).

Referring to FIG. 19, m number of vector data 1402 corresponding to the gene IDs 1401 shown in FIG. 14 are registered as m number of leaf-type cluster structures 1501 as target clusters to be joined (Step 1900). Then, cnum (the number of the clusters to be joined) and nclus (the number of the generated node-type cluster structures 1502) are initialized as "m" and "0", respectively (Step 1901). Then, cnum (the number of clusters to be joined) is judged whether it is equal to "1" or not (Step 1902). If not, the following procedure is repeated until it is equal to "1".

First, two clusters having a minimum relative distance therebetween are selected from the registered cluster structures (Step 1903). A node-type cluster structure C is newly generated (Step 1904), and the number of the node-type clusters is incremented (Step 1905). The new node-type cluster structure is registered as the $nclus^{th}$ structure of the array node_clusters[ ] (Step 1906). The two clusters selected in Step 1903 are registered as the left and right members of the new node-type cluster structure, and the distance therebetween is registered as the distance member of the new node-type cluster structure (Step 1907).

It is also possible to set up a judging basis for which one of the two clusters should be the left or right member.

Finally, the two cluster structures are removed from the target cluster structures to be joined, a new node-type cluster structure is registered (Step 1908) and the value of cnum (the number of the clusters to be joined) is decremented (Step 1909).

Figure 20:
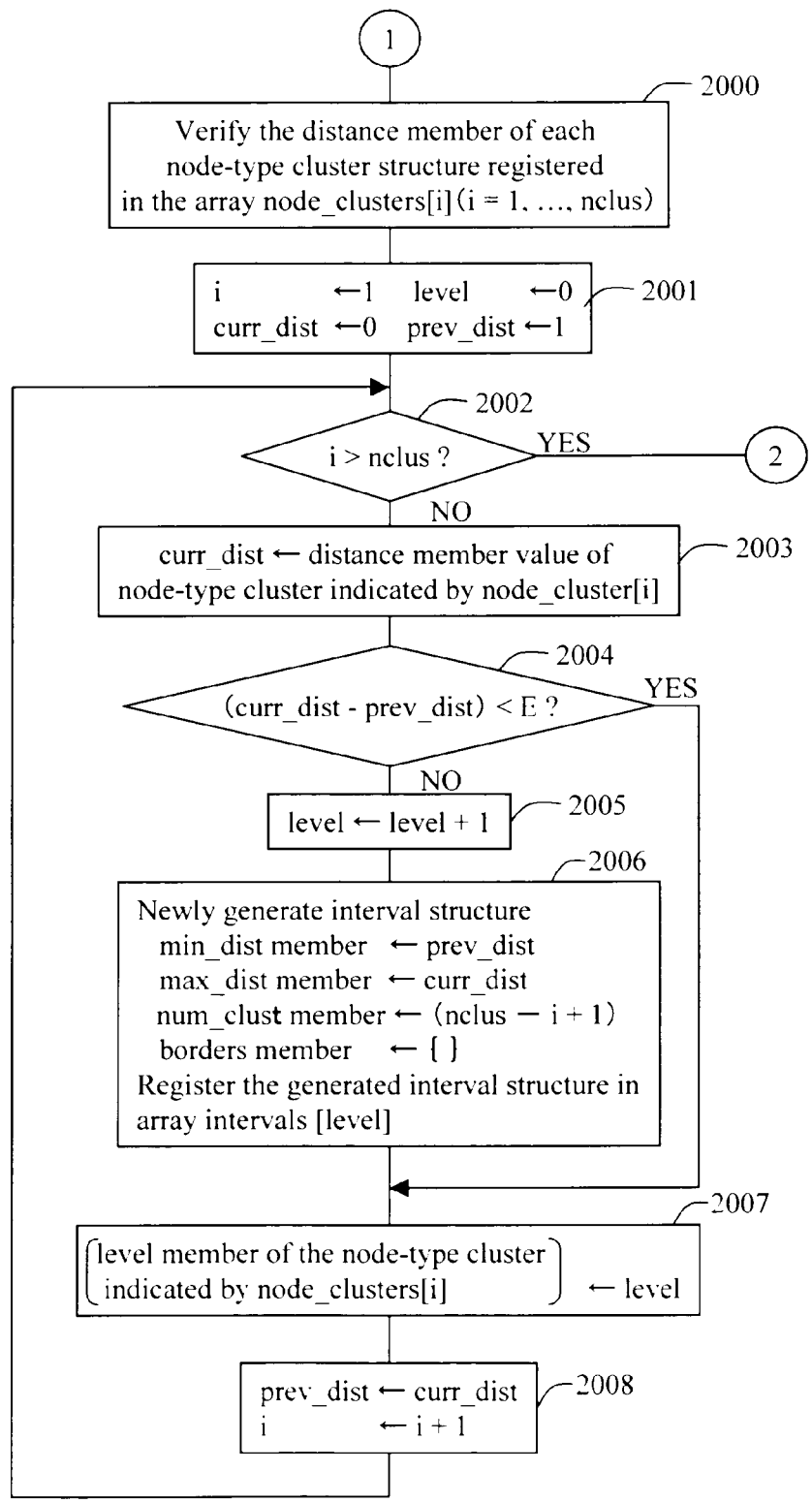
FIG. 20 is a flowchart for illustrating the clustering analysis with respect to the process of setting the cluster level.

When the value of cnum equals "1" upon the judgement of Step 1902, the process proceeds to a procedure of the flowchart shown in FIG. 20 (process of setting the cluster levels).

FIG. 20 is a flowchart for setting the cluster level (the second-stage execution).

The node-type cluster structures generated by the first-stage process are all registered in the array node_clusters[ ] (FIG. 16) and the values of their distance members are generally aligned in an ascending order according to the index of the array. However, depending on the selection of algorithm, the distance members may not be aligned in an ascending order. Thus, first, the distance member of each node-type cluster structure registered in the array node_clusters [ ] is verified (Step 2000).

When the distance members are judged that they are not aligned in an ascending order by this verification, node_clusters[ ] is subjected to a sorting process. Alternatively, only the part not in an ascending order may be detected and subjected to an additional process.

Then, each variable is initialized (Step 2001). Specifically, the variables are counter i of the array node_clusters[ ] (initial value: 1), cluster level level (initial value: 1), a value of distance member curr_dist of the presently processed node-type cluster (initial value: 0), and a value of distance member prev_dist of the previously processed node-type cluster (initial value: 0).

The value of counter i and the value of variable nclus are compared to perform the following procedure to each element of the array node_clusters[ ] (Step 2002).

First, a distance member value of an ith node-type cluster is stored as variable curr_dist (Step 2003) to judge whether or not the difference between the variables curr_dist and prev_dist is smaller than the recognition error range E determined by the user (Step 2004).

When the difference is greater than E, the variable level is incremented (Step 2005) and an interval structure is newly generated. Then, the values of prev_dist, curr_dist and (nclus−i+1) are set as min_dist, max_dist and num_clust members of the newly generated structure, respectively, and register the newly generated interval structure as a $level^{th}$ element of the array intervals[ ] (Step 2006). The borders member is provided with a null set as a default value.

When the difference between values curr_dist and prev_dist is less than E in Step 2004, steps 2005 and 2006 are omitted and the following procedure proceeds.

The value of the variable level is registered as a value of the level member of the node-type cluster structure registered in the node_clusters[i] (Step 2007).

Finally, the curr_dist value is shifted to prev_dist, the counter i is incremented (Step 2008) and the process returns to Step 2002.

Figure 21:
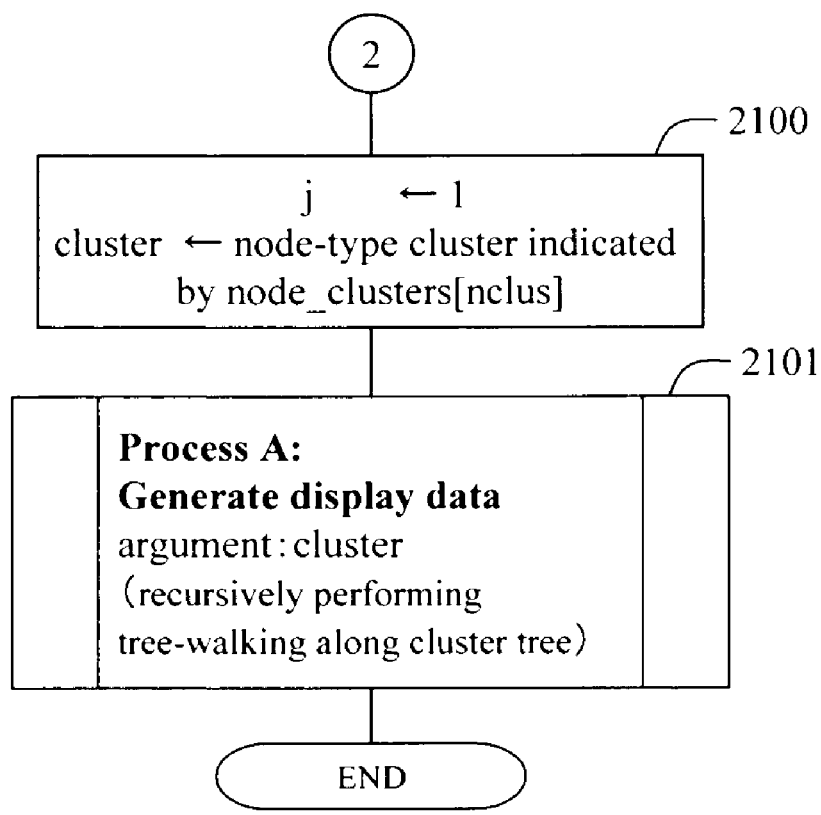
FIG. 21 is a flowchart for illustrating the clustering analysis with respect to the process of generating display data.

When all of the elements of the array node_clusters[ ] are completely subjected to the procedure of steps 2003 to 2008 (Step 2002), a procedure shown in FIG. 21 proceeds.

FIG. 21 is a flowchart showing the process of clustering analysis (Step 1802) shown in FIG. 18 in detail with respect to generating display data (the third-stage execution).

First, variable j indicating an index of array disp_leaf_clusters[ ] is set to "1", and a value of an argument cluster used for the subsequent display data generating process (Process A) is set to a node-type cluster structure indicated by the $nclus^{th}$ element of array node_clusters[ ] (Step 2100).

Then, Process A (display data generating routine) is called using cluster as an argument (Step 2101). In step 2101, Process A is recursively called to collect and calculate display data during the course of tree-walking along the tree-structure of clusters generated according to the flow-chart of FIG. 19. When this recursive process is finished, the clustering analysis is ended.

Figure 22:
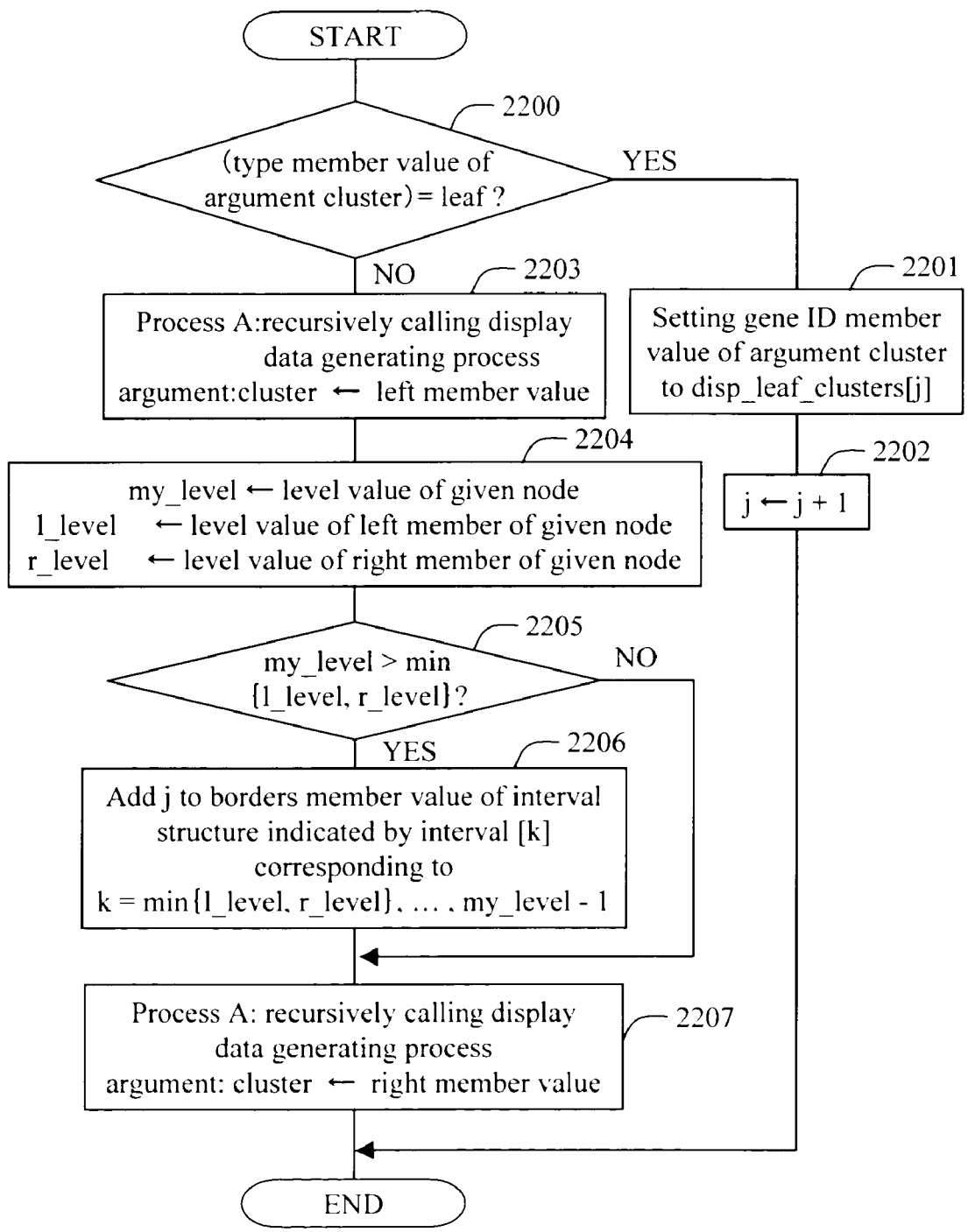
FIG. 22 is a flowchart showing Process A (in FIG. 21) of display data generation in detail.

FIG. 22 is a flowchart showing Process A (display data generating routine) (Step 2101) shown in FIG. 21 in detail.

First, a value of the type member of the cluster structure given by the argument cluster is checked (Step 2200).

When the given cluster structure is of a leaf-type, a value of the gene ID member of that cluster structure is set as $j^{th}$ element of array disp_leaf_clusters[ ] (Step 2201) and j is incremented (Step 2202).

On the other hand, when the cluster structure given by the argument cluster is of a node-type, Process A using the left member cluster as an argument is recursively called (Step 2203). Then, the given cluster is subjected to a process (Steps 2204 to 2206) and finally, Process A using the right member cluster as an argument is recursively called (Step 2207).

As to the process of the given cluster, first, the level member of the given cluster, the level member of a cluster linked via the left member and the level member value of a cluster linked via the right member are set to variables my_level, l_level and r_level, respectively (Step 2204). Then, either smaller value of l_level or r_level is compared with the value of my_level (Step 2205).

When the value of my_level is greater than the other, while index k is incremented from min{l_level, r_level} to (my_level−1), the value of the variable j is added to a set of borders member of the interval structure indicated by intervals[k] (Step 2206).

When my_level is smaller than the other upon comparison in Step 2205, process of Step 2206 is omitted and the process proceeds to Step 2207.

When the above-described series of processes performed on the leaf- and node-type cluster structures are finished, Process A is ended.

Thus, clustering analysis can be displayed as shown in FIG. 13.

First, the gene expression pattern data 1300 can be displayed line by line from the top by utilizing information of array disp_leaf_cluster[ ]. The dendrogram can be displayed based on the tree-structure data having clusters as roots indicated by node_clusters[nclus].

The phase scale bar 1301 and the dendrogram crosscutting line 1302 which are characteristic of the present embodiment can be displayed with reference to the min_dist and max_dist member values of each interval registered in array intervals[ ]. The number of the resulting gene groups 1303 can be displayed with reference to num_clust member value.

The dividing line 1304 between the displayed gene groups in the gene expression pattern data and the gene-group-specifying marks 1305 can be displayed with reference to the borders member value.

The processes shown in FIGS. 18 to 22 can be stored in a storage medium (e.g., CD-ROM) as gene expression pattern analyzing/displaying program to be provided to users via a personal computer, a work station or the like.

Herein, the result of the analysis is displayed on a display device. However, the results can be printed out with a multicolor printer which has recently been greatly improved. According to the present invention, the idea of display also comprises a printed out display.

According to the present invention, expression of a part of cell cycle can be designated to perform clustering in that region in a small range. Based on the displayed results, the user can observe the course of expression status of genes in more detail to efficiently study the biological functions of the genes from its expression status.

Furthermore, the present invention can automatically extract brief results from the entire results of clustering and select and display the results at multiple phases selectable by the user in an apprehensible manner. Thus, the user can readily judge from the display how many clusters have been grouped for studying the grouping of genes.

All publications, patents, and patent applications cited herein are incorporated herein by reference in their entirety.

What is claimed is:

1. A method for displaying gene expression patterns of multiple genes whose expressions change according to experiment cases, where a first axis represents the genes and a second axis represents gene expression status of the experiment cases, the method comprising the steps of:

designating a clustering-applied region along the second axis and a segment shorter than a width of the clustering-applied region along the second axis;

incrementally clustering the expression pattern data by the segment within the clustering-applied region in a forward or reverse direction along the second axis by calculating similarity or dissimilarity for clustering within a clustering range as wide as the segment along the second axis based on a respective reference value set for each clustering range; and displaying the results according to a predetermined display format.

2. A method for displaying gene expression patterns according to claim 1, further comprising comparing a plurality of expression patterns of every two different genes to determine whether said genes are identical or not.

3. A method for displaying gene expression patterns according to claim 2:

wherein some of the multiple genes have the same expression pattern at the beginning of said experiment cases but change to different expression patterns within the clustering-applied region along the second axis.

4. A method for displaying gene expression patterns according to claim 2:

wherein some of the multiple genes have different expression patterns at the beginning of said experiment case but change to the same expression pattern within the clustering-applied region along the second axis.

5. A method for displaying gene expression patterns according to claim 1, wherein some of the multiple genes have the same expression pattern at the beginning of said experiment cases but change to different expression patterns within the clustering-applied region along the second axis.

6. A method for displaying gene expression patterns according to claim 1, wherein some of the multiple genes have different expression patterns at the beginning of said experiment case but change to the same expression pattern within the clustering-applied region along the second axis.

7. A method for displaying gene expression patterns according to claim 1, wherein the experiment cases are conducted in a time sequence.

8. A method for displaying gene expression patterns according to claim 1, wherein the experiment cases are states of an individual's tissue.

9. A method for displaying gene expression pattern according to claim 1, wherein the experiment cases are species of individuals.

10. A method for displaying gene expression pattern according to claim 1, wherein the experiment cases are before and after drug administration.

11. An apparatus for analyzing gene expression patterns, which acquires, from a database, expression pattern data of multiple genes whose expressions change according to experiment cases, where a first axis represents the genes and a second axis represents gene expression status of the experiment cases, the apparatus comprising:

an inputting means for designating a clustering-applied region along the second axis and a segment shorter than a width of the clustering-applied region along the second axis obtained from the database, and an arithmetic unit for incrementally clustering the expression pattern data by the segment within the clustering-applied region in a forward or reverse direction along the second axis by calculating similarity or dissimilarity for clustering within a clustering range as wide as the segment along the second axis based on a respective reference value set for each clustering range; and a display means for displaying the results according to a predetermined display format.

* * * * *